US005795720A

United States Patent [19]
Henco et al.

[11] Patent Number: 5,795,720
[45] Date of Patent: Aug. 18, 1998

[54] PROCESS AND DEVICE FOR THE SEPARATION AND DETECTION OF COMPONENTS OF A MIXTURE OF MATERIALS BY TEMPERATURE GRADIENT GEL ELECTROPHORESIS

[75] Inventors: Karsten Henco, Erkrath; Detlev Riesner; Gerhard Steger, both of Düsseldorf, all of Germany

[73] Assignee: Qiagen GmbH, Hilden, Germany

[21] Appl. No.: 558,594

[22] Filed: Oct. 31, 1995

Related U.S. Application Data

[63] Continuation of Ser. No. 200,551, Feb. 22, 1994, abandoned, which is a continuation of Ser. No. 847,761, filed as PCT/EP90/01366 Aug. 18, 1990, abandoned.

[30] Foreign Application Priority Data

Aug. 19, 1989 [DE] Germany .......................... 39 27 467.5
Mar. 6, 1990 [DE] Germany .......................... 40 06 974.5

[51] Int. Cl.[6] .................................................. C12Q 1/68
[52] U.S. Cl. ................................... 435/6; 935/77; 935/78
[58] Field of Search ................................ 435/6; 935/77, 935/78, 91.2

[56] References Cited

U.S. PATENT DOCUMENTS

| 4,671,870 | 6/1987 | Tompa et al. ........................... 210/149 |
| 5,066,377 | 11/1991 | Rosenbaum et al. ................. 204/182.8 |

FOREIGN PATENT DOCUMENTS

| 0198207 | 3/1986 | European Pat. Off. . |
| 0318273 | 5/1989 | European Pat. Off. . |

OTHER PUBLICATIONS

Val C. Sheffield et al., "Attachment of a 40-base pair G+C–rich sequence (GC–clamp) to genomic DNA fragments by the polymerase chain . . . " Proc. Natl. Acad. Sci., USA, vol. 86, pp. 232–236, 1989.

Ann–Christine Sylvanen et al., "Quantification of polymerase chain reaction products by affinity–based hybrid collection", Nucleic Acids Research, vol. 16, No. 23, pp. 11327–11338, 1988.

Roger M. Wartell et al., "Detecting base pair substitutions in DNA fragments by temperature–gradient gel electrophoresis", Nucleic Acids Research, vol. 18, No. 9, pp. 2699–2705, 1990.

Richard M. Myers et al., "Nearly all single base substitutions in DNA fragments joined to a GC–clamp can be detected by . . . ", Nucleic Acids Research, vol. 13, No. 9, pp. 3131–3145, 1985.

Richard M. Myers et al., "Detection & Localization of Single Base Changes by Denaturing Gradient Gel Electrophoresis", Methods in Enzymology, vol. 155, pp. 501–527, 1987.

Detlev Riesner et al., "Temperature–gradient gel electrophoresis of nucleic acids: Analysis of conformational transitions, sequence variations, . . . ", Electrophoresis, vol. 10 (5–6), pp. 377–389, 1989.

*Primary Examiner*—Lisa B. Arthur
*Attorney, Agent, or Firm*—Jacobson, Price, Holman & Stern, PLLC

[57] ABSTRACT

The invention relates to a process for the separation and detection of components of a mixture of materials by temperature gradient gel electrophoresis, wherein either

- a spatial temperature gradient is built up by spatially separated temperature levels, or
- a time temperature gradient, or
- a temperature gradient is built up by combination of spatial and timewise temperature gradient.

The temperature levels for building up the spatial temperature gradient are adjusted by controllable heating or cooling devices.

To build up the time temperature gradient, the temperature level at each point of the separation path within the separation medium may be optionally adjusted time-dependently by means of controllable heating or cooling devices. There is described a device for performing the process with controllable heating or cooling devices to build up temperature gradients, a hollow body arranged between the temperature levels which contains the medium used for separation, and a thermostat jacket enclosing the hollow body.

12 Claims, 16 Drawing Sheets

```
          R1=BamH1    G-C-clamp                    primer 1a*
        5'CCGGATCCCGCCGCCCGCCCCGCGCCCTGCCGTTACTGCCCTG
62200                                 . . . . . . . . . . . . . . . .
        ACACCATGGTGCACCTGACTCCTGAGGAGAAGTCTGCCGTTACTGCCCTG
        TGTGGTACCACGTGGACTGAGGACTCCTCTTCAGACGGCAATGACGGGAC TGG-3'
        . . .
        TGGGGCAAGGTGAACGTGGATGAAGTTGGTGGTGAGGCCCTGGGCAGGTT
        ACCCCGTTCCACTTGCACCTACTTCAACCACCACTCCGGGACCCGTCCAA
                                                 exon 1 | intron 1
     IVS-1-6
         C
         |
        GGTATCAAGGTTACAAGACAGGTTTAAGGAGACCAATAGAAACTGGGCAT
        CCATAGTTCCAATGTTCTGTCCAAATTCCTCTGGTTATCTTTGACCCGTA
                          . . . . . . . . . . . . . . . . . . . .
                          GTCCAAATTCCTCTGGTTATCTTAAGCG-5'
                            primer 1b              R2=EcoR1
62350
        GTGGAGACAGAGAAGACTCTTGGGTTTCTGATAGGCACTGACTCTCTCTG
        CACCTCTGTCTCTTCTGAGAACCCAAAGACTATCCGTGACTGAGAGAGAC
```

FIG. 2

DUBO : [USERS.STEGER.SEQ]HUMHBB_PREMRNA.LIS;3
GenBank : HUMHBB 62155 - 63760 : pre-mRNA
         62205 - 62296 : Exon1
         62427 - 62649 : Exon2
         63500 - 63628 : Exon3
This file: 62155 - 62649 =  1 - 495
                           51 - 142 : Exon2
                          272 - 495 : Exon3

FIG. 3

```
  1   ACATTTGCTT CTGACACAAC TGTGTTCACT AGCAACCTCA AACAGACACC
 51   ATGGTGCACC TGACTCCTGA GGAGAAGTCT GCCGTTACTG CCCTGTGGGG
101   CAAGGTGAAC GTGGATGAAG TTGGTGGTGA GGCCCTGGGC AGGTTGGTAT
151   CAAGGTTACA AGACAGGTTT AAGGAGACCA ATAGAAACTG GGCATGTGGA
201   GACAGAGAAG ACTCTTGGGT TTCTGATAGG CACTGACTCT CTCTGCCTAT
251   TGGTCTATTT TCCCACCCTT AGGCTGCTGG TGGTCTACCC TTGGACCCAG
301   AGGTTCTTTG AGTCCTTTGG GGATCTGTCC ACTCCTGATG CTGTTATGGG
351   CAACCCTAAG GTGAAGGCTC ATGGCAAGAA AGTGCTCGGT GCCTTTAGTG
401   ATGGCCTGGC TCACCTGGAC AACCTCAAGG GCACCTTTGC CACACTGAGT
451   GAGCTGCACT GTGACAAGCT GCACGTGGAT CCTGAGAACT TCAGG
```

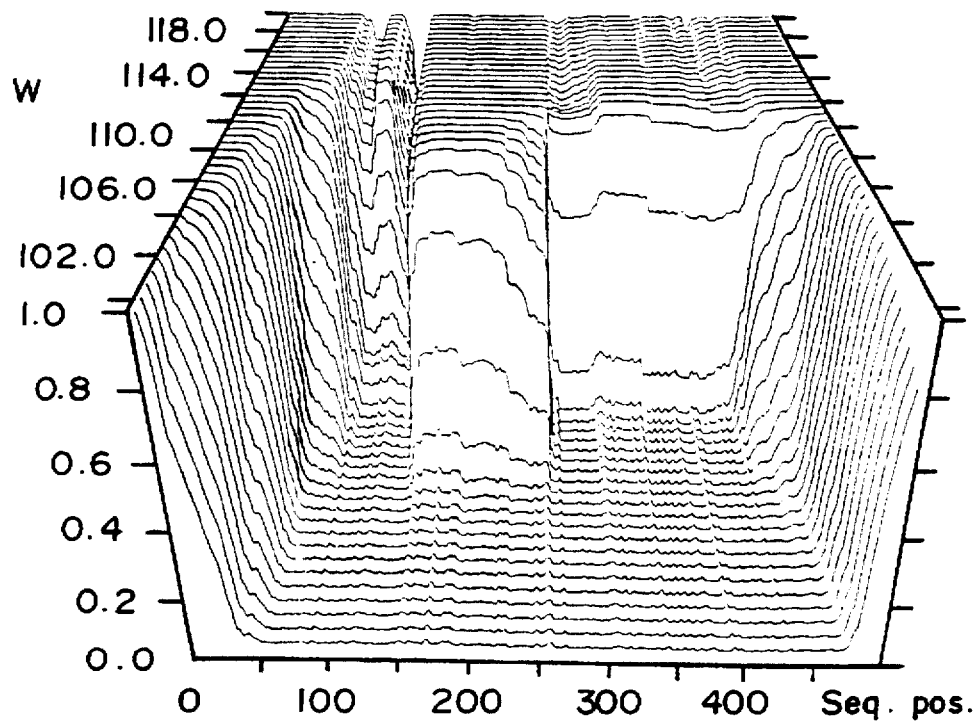

FIG. 4
DUBO : [USERS.STEGER.SEQ]KARSTEN9.LIS;1
125 GenBank:HUMHBB GC-clamp + P1a/62233-62338(=P1b)
CCGCCGCCCGCCCCGCGCC-
CTGCCGTTACTGCCCTGTGGGCAAGGTGAACGTGGATGAAGTTGGTGGTGAGGCCCTGGGCAGGTTGGTATCAAGGTTACAAGACAGGTTTAAGGAGACCAATAG
pot. mut. at 62302(= position 89) : T -> C
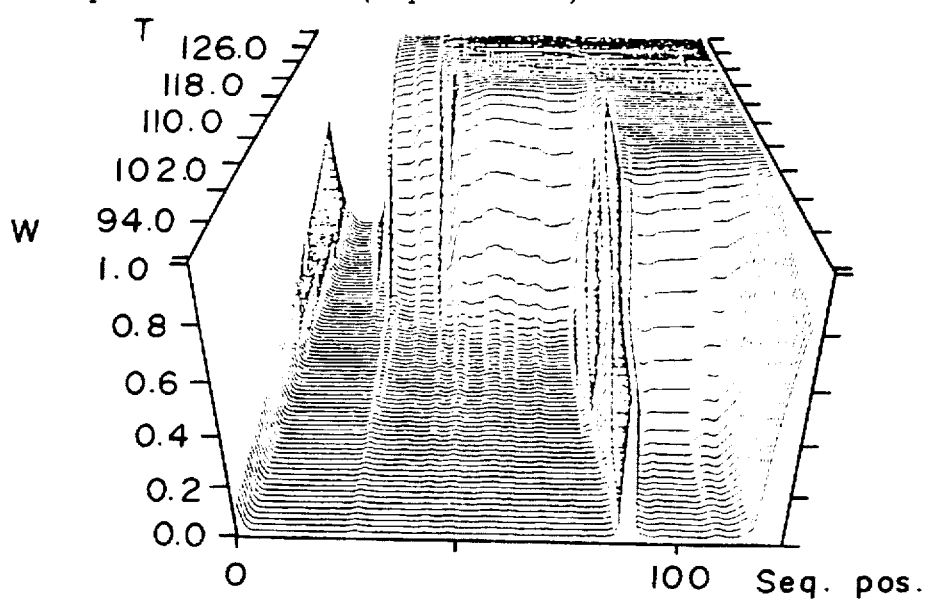
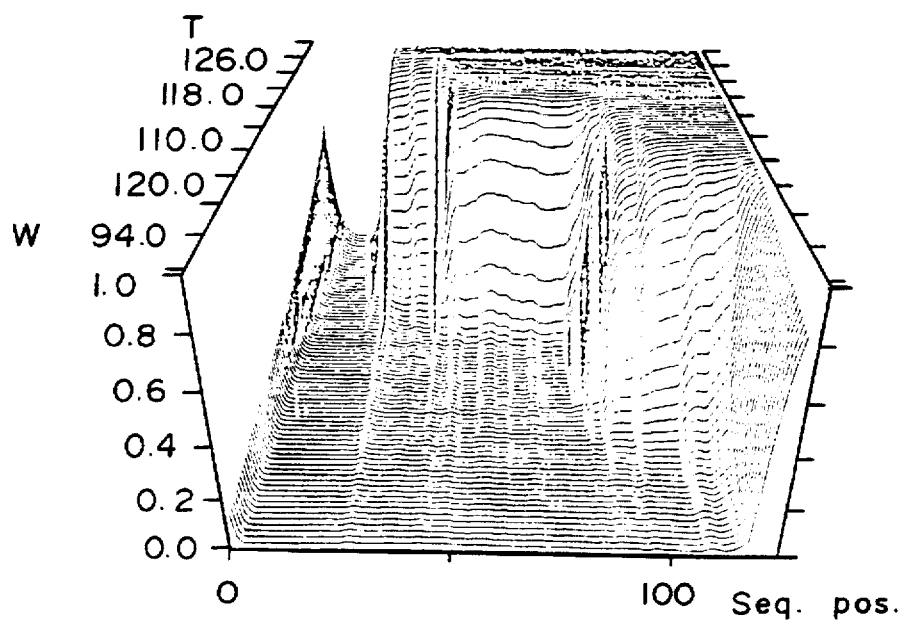

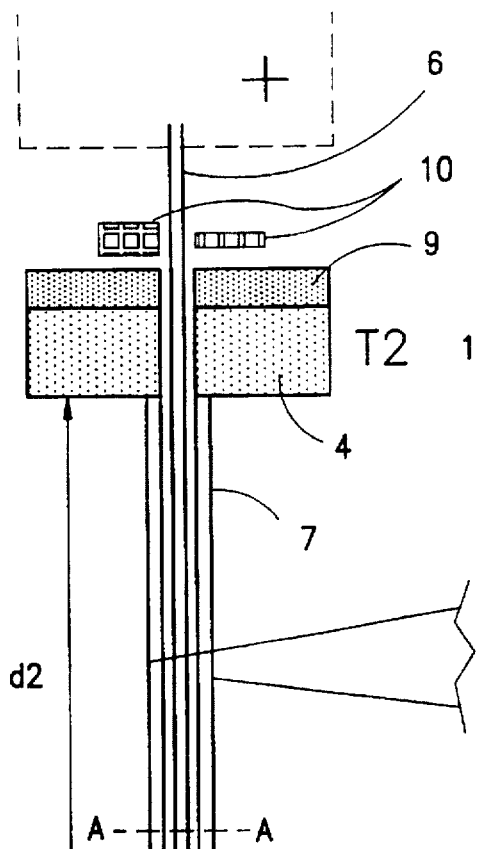
FIG. 10
$$T = T2 - (T2 - T1) \times d2/d1 + d2$$
FIG. 10a
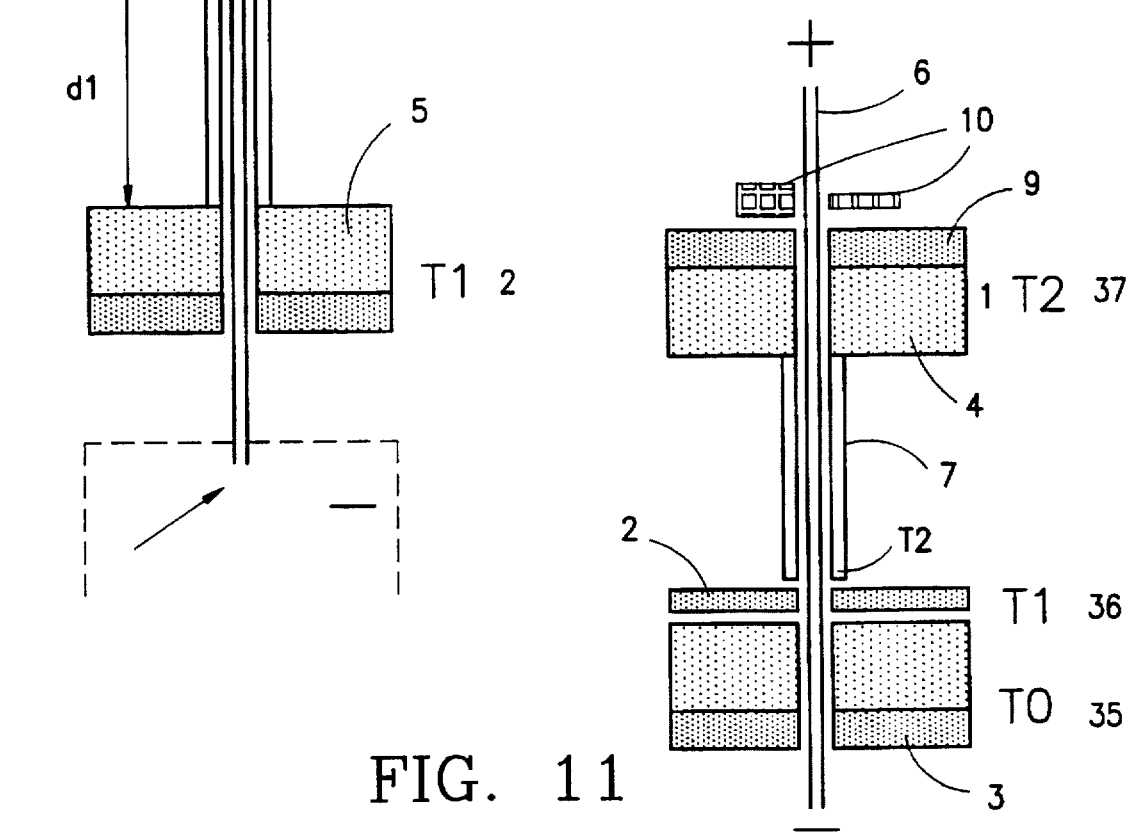
FIG. 11

Multichannel Version in Microtiter Format

FIG. 16a
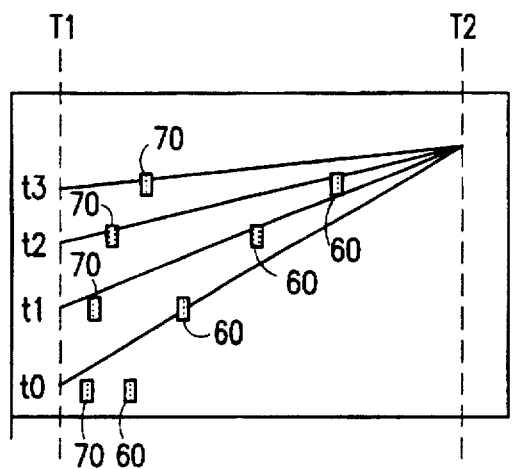
FIG. 16b
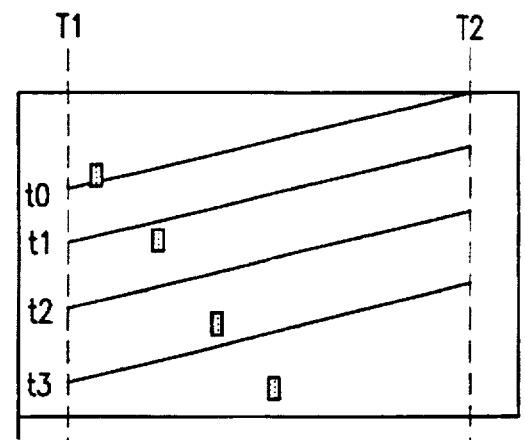
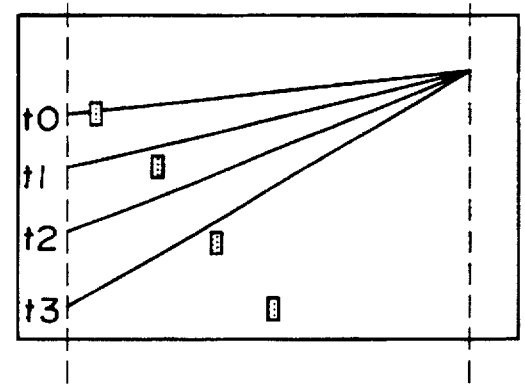
FIG. 16c
Migration direction

PROCESS AND DEVICE FOR THE SEPARATION AND DETECTION OF COMPONENTS OF A MIXTURE OF MATERIALS BY TEMPERATURE GRADIENT GEL ELECTROPHORESIS

This application is a continuation of U.S. application Ser. No. 08/200,551, filed Feb. 22, 1994, abandoned, which is a continuation of U.S. application Ser. No. 07/847,761, filed Feb. 19, 1992, abandoned, which is a continuation-in-part of PCT Application No. PCT/EP90/01366, filed Aug. 18, 1990, abandoned.

FIELD OF THE INVENTION

Subject matter of the present invention is a process for the separation and detection of components of a mixture of materials by temperature gradient gel electrophoresis, in particular, a process for the detection of mutations of nucleic acid fragments by analysis of the heteroduplex obtained by hybridization of the nucleic acid fragment having the mutation (mutant) and the nucleic acid fragment not having the mutation (wild type), a process for sample preparation using an oligonucleotide as well as this oligonucleotide itself, and a device for performing the temperature gradient gel electrophoresis.

BACKGROUND OF THE INVENTION

Detection of mutations in genetic material or detection of phenotypical consequences of genetic mutation is an important analytical object in many fields of biological research, applied medicine, biotechnical production and criminology. On a genetic level, mutation means exchange of at least one nucleotide or base pair on the DNA or RNA level. The potential of the so-called "genetic engineering" using hybridization or sequencing techniques allows for the detection of a mutation in clonal DNA or RNA. However, these techniques are restricted to research-related use. For routine employment, a technical standard capable of standing comparison with immunological methods (ELISA, etc.), could not be achieved.

Temperature gradient gel electrophoresis, as described in German Application DE-OS 36 22 591, is a method for detecting slight structural differences or peculiarities of biological macro-molecules such as nucleic acids or proteins. However, this technique is not suitable for automatable analysis, as is necessary, for example, in the determination of many individual samples in the clinical field for the analysis of genetic diseases or in forensic analytics. Using temperature gradient gel electrophoresis technology, it was possible to make mutations visible without tedious differential hybridization (Riesner et al. (1989), Electrophoresis 10, p. 377–389); this technique, however, is restricted to the operation of flat-bed gel electrophoresis for research analytics. Similar results are obtained with the combination of flat-bed gel electrophoresis and a denaturing chemical gradient which, however, can hardly be formed in reproducible fashion and, thus, is out of question for automatization.

The necessary precondition for the sensitive detection of even single mutations in temperature gradient gel electrophoresis is a homogeneous temperature level within the gel perpendicular to the electrophoresis flow direction, i.e., at points of equal electrical potential. For instance, this cannot be realized sufficiently by using double-side thermostatted vertical electrophoresis according to D. R. Thatcher and B. Hodson (1981), Biochemistry 197, p. 105–109, since the thermostat plates in opposition to each other which are insufficiently thermally connected do not have identical temperatures at points of equal electrical potential.

The appearance of living nature is programmed on a genetic level in the form of nucleic acids consisting either of RNA or DNA chain molecules. Changes of genetic information are referred to as mutations and are the basis for evolutionary developments, for genetically caused diseases, and other genetically caused biological properties of a virus or an organism. Most of the mutations having occurred do not have notable consequences for the system. Such mutations are referred to as neutral. Once gene-technological techniques had been introduced, it has become possible to discover a mutation, to determine when it was created, and to measure its influence on a biological function.

Using the technique of comparative sequence analysis (sequencing) of homologous sequences, a mutation can be recognized. The term mutation is understood to be a single nucleotide exchange, a deletion, or an insertion of single up to many nucleotides, or a rearrangement of chain segments. In spite of great progress in recent years, sequence analysis still is a costly technique, supported by expensive equipment, and not suited for routine analysis. Merely the search for per se known mutations described for certain genetic diseases, for example, α-1-antitrypsin deficiency (Kidd, U. J., Wallace, R. B., Hakura, K., and Woo, S. L. C. (1983), Nature 304, 230–234), has been technically simplified by the use of synthetic oligonucleotide probes. A number of questions, however, are nearly completely reluctant to experimental access, such as, for example, the search for unknown mutations in long gene segments not being associated with restriction fragment length polymorphisms (RFLP), or routine examinations important to medical genetics, population analysis, evolutionary relationship analysis, analysis of virus variants, etc.

Nucleic acid chains (RNA and DNA) are capable of forming double-helical structures with so-called complementary sequences, resulting in DNA/DNA, RNA/RNA, and DNA/RNA double-stranded structures. A characteristic feature of these structures is temperature-dependent denaturation (melting) of the double-strands. Melting occurs within a very narrow temperature interval, i.e., large sections of the double-stranded structures are denatured in a single-step process. Thus, it is a physical reaction taking its course in a highly cooperative manner. Loss of continuous double-stranded structure becomes manifest in mobility change (in most cases loss of mobility) of the nucleic acid concerned. Such mobility loss may be used in an electrophoretic separation process, to separate nucleic acids having different melting temperatures. Thus, thermodynamically less stable nucleic acids migrate more slowly and, therefore, less far than those having stable structures. Here, the medium used for separation must have a denaturation gradient, for instance by increasing concentration of a denaturing agent. Stability of the internal regions of base pairs depends on G/C content and on the sequence. These effects have been studied in detail (Meinkoth, S. and Wahl, G. (1984), Analytical Biochem. 138, 267–284).

Now, if mutation leads to sufficient changes in the according region, the mutated nucleic acid will exhibit different melting behavior than the non-mutated one. Frequently, a mutation is characterized by the exchange of only one base pair for another (transversion or transition). Therefore, the mutated nucleic acid strand is quite stable in itself and, in general, melts at similar temperatures as does the non-mutated form, so that discrimination is not possible. Such mutations, however, become visible by mixing the mutated nucleic acid and a nucleic acid not having this mutation (wild type) with comparable concentrations, denaturing including separation of strands, and subsequent renaturing. In this way, all combinations of the corresponding nucleic acid single-strands are formed, including, among other, so-called heteroduplexes from mutated single-strands and non-mutated single-strands. Now, since each nucleotide in these heteroduplexes lacks the complementary nucleotide at the site of mutation, notable destabilization within the neighbor double-helix regions occurs at these positions. Accordingly, these heteroduplexes will melt more readily than wild type or mutant duplexes.

Disadvantageously, the procedures existing hitherto are relatively tedious in handling, and discovery of presumable mutations is not always guaranteed.

Thus, the technical problem which the invention is based upon is, on the one hand, to provide a process that overcomes the disadvantages of impracticability of the temperature gradient gel electrophoresis for analytical routine operation and renders the temperature gradient gel electrophoresis easier to handle on the whole. Furthermore, a device is to be provided allowing for automatic temperature gradient gel electrophoresis evaluation. This device also is intended to permit simultaneous analysis of nucleic acids strongly varying in structure. Another technical problem is improvement in discovery, in particular, quantitative and/or qualitative detection of mutations and/or gene variants. Moreover, the improvement, in a specific embodiment, is to ensure simple and safe sample preparation.

SUMMARY OF THE INVENTION

These technical problems are solved by a process for the separation and detection of components of a mixture of materials by temperature gradient gel electrophoresis, comprising either:

building up a spatial temperature gradient in direction of the electrical field used for separation by at least two spatially separated temperature levels, or building up a time temperature gradient by varying the temperature of a temperature level over time, or building up a time temperature gradient by combining spatial and timewise temperature gradient, transferring the temperature gradient into the gel matrix in a conducting fashion, adjusting the temperature levels for building up the spatial temperature gradient by controllable heating or cooling devices, with points of equal electrical potential having identical temperatures, or optionally adjusting the temperature level, depending on time, by using one or several controllable heating or cooling devices for building up the time temperature gradient at each point of the separation path within the separation medium, and if appropriate, detecting the separated components at the end of the separation path.

DETAILED DESCRIPTION OF THE INVENTION

Figure 1:
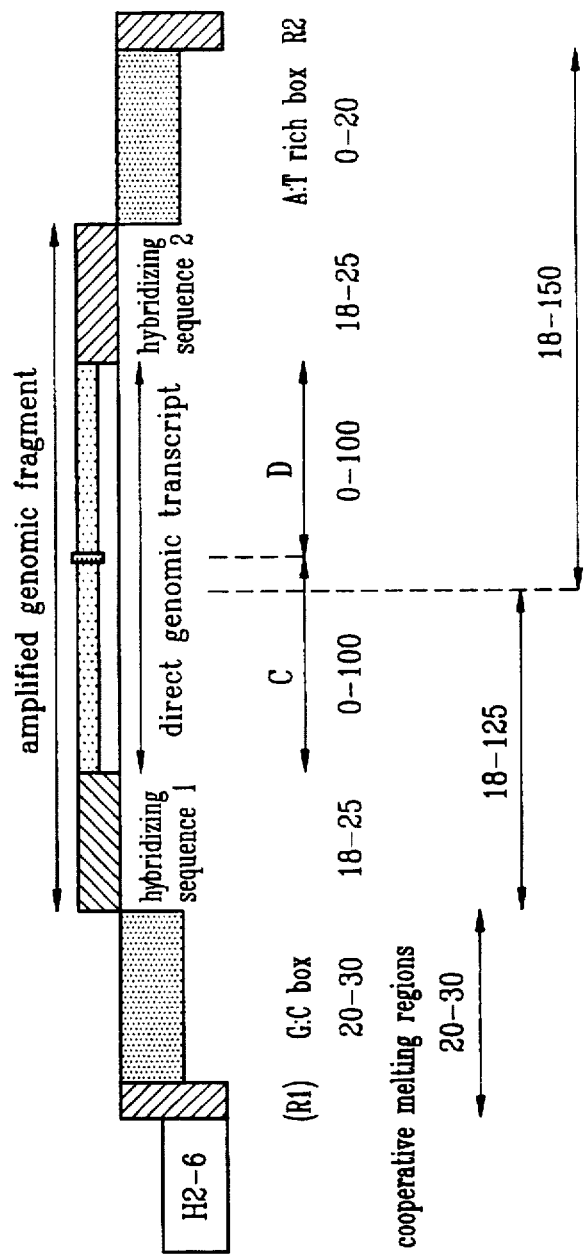

In a preferred embodiment, detection of nucleic acid mutations is performed quantitatively and qualitatively, namely by analysis of the heteroduplex obtained by hybridization of the nucleic acid fragment having the mutation (mutant) and the nucleic acid fragment not having the mutation (wild type), the nucleic acid fragment to be examined and bearing the mutation being selected in such fashion that the mutation is located in a thermodynamically unstable region of the heteroduplex.

According to a further preferred embodiment, the present invention relates to a process for the quantitative and qualitative detection of mutants or specific gene sequences, wherein, to a mixture of differing sequences of which one concentration may be known, there is added an inferior amount of a marker nucleic acid molecule, the sequence of which is identical to the sequence of one of the above sequences except for the mark, and the mixture is subjected to at least one denaturation/renaturation cycle and analyzed. Preferably, the sequence of the marked nucleic acid is identical to the sequence of that nucleic acid of a known concentration, except for the mark. Additionally, it is preferred that the hybrids formed after a denaturation/renaturation cycle are separated by temperature gradient gel electrophoresis and their relative signal intensities are measured, and that the nucleic acids to be analyzed have been obtained by enzymatic amplification.

The present invention further includes a device for performing the temperature gradient gel electrophoresis, characterized in that between at least two heating or cooling devices (1, 2) building up a temperature gradient and having a heat reservoir (4, 5), with more than two heating or cooling devices, between the most distant heating or cooling devices, there is arranged a hollow body (6) penetrating the heating or cooling devices and containing in its lumen the separation medium used for separation, and the hollow body (6) is enclosed by heat-conducting thermostatting jacket (7).

Preferred embodiments of the device include the following:

The hollow body (6) is a cylindrical capillary.

Between the outer wall of hollow body (6) and the inner wall of thermostat jacket (7), there is provided a heat exchanger (8), and preferably, the heat exchanger (8) consists of a viscous liquid.

The heating or cooling devices have a thermostatted liquid bath and Peltier heating elements (9) or electrical heating elements and/or a heat reservoir (4, 5).

The thermostat jacket (7) is connected to all the heating or cooling devices (1, 2) in a heat-conducting fashion.

A third heating or cooling device (3) is provided at the sample application side.

The thermostat jacket (7) is thermally decoupled from the second device (2).

The heating or cooling devices (1, 2) are time-controllable.

The heating or cooling devices (1, 2) having corresponding heat reservoirs (4, 5) accommodate a multiplicity of hollow bodies (6), in that the devices (1, 2) and (4, 5) are designed in the form of blocks (4a, 5a) and have a multiplicity of drillings (11) across which the hollow bodies (6) are arranged in a penetrating fashion.

The hollow bodies (6) at the end sides project from the devices designed in the form of blocks (4a, 5a).

The spatial temperature gradient of the process according to the invention may be built up in such fashion that, using a controllable heating or cooling device, a specified temperature level is adjusted at the sample side, while the second, spatially separated temperature level is defined by the temperature of the electrophoresis bath at the opposite side. So simple a procedure is possible where the electrophoresis bath is dimensioned so that the temperature remains constant. To do that, an electrophoresis bath of sufficiently large dimensions is necessary. But here, too, the second temperature level preferably is designed controllable, for instance by Peltier elements, heating wires, or water baths capable of being thermostatted.

After applying the samples, the components of the material mixture to be separated will migrate into the separation medium in the direction of the electrical field. They will reach the first temperature level and experience a conformational transformation resulting in a dramatic reduction of migration velocity. This is effected either by the adjusted temperature or in combination with partially denaturing agents. In case the components to be separated are, for example, nucleic acids, part of the double-strands are widened by the partial denaturation to give larger loops which virtually get stuck in the separation medium and are no longer capable of following the electrophoresis. Now, when the temperature is decreased, the loop regions are regenerated depending on their thermodynamic stability whereby mobility of the nucleic acids in the separation medium is increased again. The corresponding temperature is a material characteristic of the respective nucleic acid. Thus, separation of different components, depending on temperature, can be achieved. Those molecules where mobility has been increased migrate across the separation path and may be detected at the electrophoresis target pole.

Likewise, it is possible to build up a temperature gradient having increasing temperature in electrophoresis direction wherein the molecules are initially separated according to their thermodynamically partial melting behavior in that separation medium. At lower temperatures, the thermodynamically most unstable structures will in part thermally denature at first, with nucleic acids, for example, by formation of loop regions. Mobility of these nucleic acids will be decreased dramatically, so that these either "get stuck" in the separation medium or at least will migrate much more slowly. The other components further migrate through the separation medium until each of their specific denaturation will result in dramatic loss of mobility of each molecule in the separation medium. Specifically selecting the separation gel mesh size, the residual mobility of the virtually locked biomolecules after some time—though a very long time—enables all components of the mixture to be separated to migrate across the separation path. This effect is supported by the fact that, with complete denaturation, i.e., separation into single-strands, mobility of the partially denatured nucleic acids dramatically increases again, since at this point, only single-strands migrate across the separation medium. While the thermodynamically most unstable nucleic acids losing their mobility already at low temperature further migrate in the gel very slowly, they eventually reach a higher temperature level, however, giving rise to complete melting, so that the double-strands break down to give single-strands. This results in enhanced migration velocity as described above.

This effect may also be utilized for overall electrophoresis enhancement. Once the components have been separated from each other by partial denaturation and loss of mobility in the separation medium, the temperature level of the entire separation medium may be increased above the melting point of the double-strands to convert all of the double-strands completely to single-strands. After this, all the components will regain their mobility. To carry out this procedure, it is necessary, however, that the temperature be equilibrated very rapidly within the entire separation medium, or the electrophoresis is interrupted until temperature equilibration is reached, for instance, by switching off the electrical field. Preferably, the molecules to be separated are similar in size. The procedure, with the conditions described, then ensures that, in performing isothermal electrophoresis using high temperature levels, the separated components maintain their relative spatial distance in the further course of electrophoresis.

Another procedure merely uses a time-controlled variable temperature program, preferably at the sample input side of the electrophoresis, to build up a time temperature gradient leading to separation of the components of the material mixture. Initially, the sample to be separated is allowed to migrate electrophoretically into the separation medium. The temperature level at the side of sample input is selected such that with nucleic acids, for example, the double-strands are widened to give loops without being completely molten down, however. The formation of loops may be supported by appropriate selection of reagents. This results in a quasi locking of the components to be analyzed in the separation medium at the beginning of the electrophoresis. On sectionwise decrease of temperature, the thermodynamically most stable double-strands are regenerated, so that these nucleic acids exhibit enhanced mobility. Then, they begin to migrate across the separation gel. Due to subsequent temperature variation, the nucleic acids of next lower thermodynamic stability will subsequently begin to migrate. It may be advantageous to conduct the temperature decrease stepwise so as to enhance the separation effect in spatial terms. The molecules beginning migration virtually gain a spatial lead during migration across the separation medium. With sufficiently different thermodynamic stabilities, it is also possible, however, to continuously decrease the temperature gradient relatively fast. Using this procedure, it may be advantageous to provide an electrophoresis end point with a controllable heating and cooling device as well.

In all the procedures according to the invention, it is necessary, however, to enclose the separation medium with a thermally conductive thermostat jacket to build up a reproducible temperature gradient or reproducible isothermal conditions. To build up the reproducible temperature gradient or isothermal temperature level, it is absolutely necessary that the energy flow in the thermostat jacket be small compared to energy flow in the heating and cooling element.

The temperatures useful for temperature gradient gel electrophoresis are preferably in the range of from 0° to 100° C. Preferably, the separation medium consists of polyacrylamide gels.

The technical problem of detecting components of a mixture of materials, the mixture consisting of nucleic acids which, in particular, exhibit only one mutation, is solved by a process wherein detection of nucleic acid mutations is performed quantitatively and qualitatively, namely by analysis of the heteroduplex obtained by hybridization of the nucleic acid fragment having the mutation (mutant) and the nucleic acid fragment not having the mutation (wild type), the nucleic acid fragment to be examined and bearing the mutation being selected in such fashion that the mutation is located in a thermodynamically unstable region of the heteroduplex.

Further features of this preferred embodiment include the following:

Selection of the thermodynamically unstable region containing the mutation is done by calculation.

The nucleic acid fragment to be examined is chosen such that the mutation is located in the least thermodynamically stable region.

The more thermodynamically stable region of the nucleic acid fragment has terminal oligo G and/or oligo C nucleotides, wherein the number of G and/or C nucleotides is preferably from 20 to 30.

The nucleic acids are amplified by polymerase chain reaction (PCR).

Two oligonucleotides are used which hybridize to the DNA to be amplified in immediate proximity.

After sample preparation, the heteroduplexes to be examined are subjected to temperature gradient gel electrophoresis.

The temperature gradient is oriented perpendicularly to the direction of the electrical field, or, alternately, the temperature gradient is oriented parallel to the direction of the electrical field.

The temperature gradient is varied with time.

The temperature gradient is set off at the cathode side of the electrical field from a temperature level higher than the melting point of the thermodynamically unstable region of the heteroduplexes, and is time-controlled in the direction of the level of the lower temperature level at the anode side.

The anode side temperature level of the static temperature gradient is higher than the temperature level at the cathode side.

The cathode side temperature level of the static temperature gradient is higher than the temperature level at the anode side.

For this embodiment, an oligonucleotide having 5' terminal affinity groups is preferably used as a so-called primer to start the polymerase chain reaction (PCR) (Saiki et al. (1985), Science 230, 1530–1534). In this oligonucleotide, from two to eight histidine residues may be 5'-terminally bound as affinity groups, wherein the preferred number of histidine residues is six, or biotinyl residues are 5'-terminally bound as affinity groups. It is further preferred that the oligonucleotide additionally contains a restriction site and/or a G/C-rich box and/or an A/T-rich box, and a sequence hybridizing with the nucleic acid sequence to be examined.

A special embodiment of the process according to the invention employs the oligonucleotide described above. According to this embodiment, the nucleic acid bearing the mutation is amplified using an oligonucleotide having 5'-terminal activity which is bound to a material affixed to solid phase and having affinity to the affinity groups of the oligonucleotides, then, optionally, in the presence of marked nucleic acid single- or double-strands not having the mutation, subjected to at least one denaturation/renaturation cycle, eluted subsequently, and thereafter, subjected to the separation process. Preferred aspects of this embodiment include the following:

The material having affinity to the affinity group of the oligonucleotide is a polymeric support containing a chelate of a chelating agent and a transition metal ion.

Preferably, the material having affinity to the affinity group of the oligonucleotide is a polymeric support containing a chelate of nitrilotriacetic acid covalently bound to the support and Nickel2+.

The material having affinity to the affinity group of the oligonucleotide is a polymeric support having covalently bound avidin or streptavidin.

The polymeric support is a membrane or a particle-shaped material.

The process according to the invention can be used to for discovering and characterizing mutations in DNA or RNA such as punctual mutations, deletions, insertions, and rearrangements of the nucleic chain. The sample material can be derived from living and dead fossil tissue, and tissue no longer metabolization-active in vivo. The process can further be used for conducting genetic studies such as forensic analytics; elucidation of hereditary diseases and/or genetically characterized anomalies; analytics of individuals, finger printing; for carrying out fine characterization of lineage deviations in industrial microbiology, in medicinally relevant pathogens, in viruses, particularly in viruses known for frequent mutations, bacteria, fungi and protozoans; for preforming studies of evolutionary development; or for the preparation of discovered mutants, where a mutant is tracked down as a single band in the detection unit, and is isolated directly or by changing the direction of the voltage gradient within an electrical elution, directly PCR-amplified or directly sequenced and/or cloned; or for determining and assigning individuals, where genetically amplified gene segments, particularly those from single-copy regions of the genome, are hybridized with a homogenous standard segment, or hybridized with homologous sequences of a DNA to be tested for identity of the corresponding individual and genetically amplified in an analogous fashion.

Preferred materials for performing the process include the following:

A mixture of reagents and one or more marked nucleic acid probes, a partially or completely homologous standard nucleic acid in non-marked form, and a hybridization buffer allowing for denaturation and renaturation of double-strand structures in the temperature range between 0° and 100° C.

A mixture of at least one marked nucleic acid probe, a partially or completely homologous standard nucleic acid in non-marked form, and a hybridization buffer allowing for denaturation and renaturation of double-strand structures in the temperature range between 0° and 100° C., wherein the mixture preferably contains a solid-phase carrier including the oligonucleotide having 5'-terminal activity described above, whereby amplified segments may be directly withdrawn from the reaction mixture.

The detection process according to the invention for mutation in mixtures of nucleic acids is explained in more detail below.

Initially, the nucleic acid fragment suitable for mutation analysis is cut to appropriate size, with the mutation being located in a thermodynamically labile region. This region may be determined by either experiment or calculation. If necessary, the nucleic acid fragment may be amplified by PCR (polymerase chain reaction), the thermodynamically more stable region being preferably stabilized in such fashion that it maintains stability under maximum denaturing conditions of the analytical experiment. The nucleic acid fragment then does not melt down to complete strand separation but forms a Y-shaped structure of low electrophoretic mobility. In particular, such stabilization may be effected by adding a region of stabilizing G/C nucleotides or non-charged nucleotides. The stabilizing influence of more than 40 G/C base pairs has been described by Sheffield, V.C. et al. (1989) Proc.Natl.Acad.Sci. USA 86, 232–236. Surprisingly, however, as few as 20 to 30 G/C base pairs have been shown to provide sufficient stabilization. Preferably, temperature gradient gel electrophoresis is used as described according to the invention. Nonetheless, the process of German Application DE-OS 36 22 591 may be used as well, wherein the temperature gradient is formed in a plate electrophoresis device and separation is conducted using a gel arranged on a plate.

In case certain nucleic acid fragments are to be multiplied by amplification reactions such as the so-called PCR (polymerase chain reaction), oligonucleotides are used as so-called primers. These primers are selected such as to be capable to hybridize with part of the nucleic acid to be examined. Advantageously, the probes are to hybridize with the terminal regions of the nucleic acid to be examined. Furthermore, it is desirable to provide the primers with restriction sites to be able to incorporate the amplified segments into vectors. In another preferred embodiment the primers have terminal chemical groups that may serve as affinity ligands.

FIG. 1 schematically represents a particularly preferred oligonucleotide which may be used as primer in a PCR. The primer Hnp1 consists of a hybridizing sequence 1 having about 18 to 25 nucleotides. Towards the free end, a G/C box of preferably from 20 to 30 nucleotides follows succeeded by a restriction site and one or more chemical groups that may serve as affinity ligands. The primer p2 likewise consists of a hybridizing sequence 2, an A/T-rich box of from 0 to 20 nucleotides length, and a restriction site R2. In case of mutant analysis within highly polymorphic regions, it is recommended to keep the regions C, D (FIG. 10) as small as possible, in extreme cases to 0 nucleotides, to detect just one polymorphic position. This is exemplified using the example of probe construction to detect β-globin thalassaemia "Yugo" (IVS-1-6, T-C).

An important type of β-globin thalassaemia is the splicing mutant (IVS-1-6, T-C) on the β-globin locus. This mutation prevents correct splicing between exon 1 and exon 2. The environment of the mutated gene location IVS-1-6 is represented in FIG. 2. There is shown a sector of human βgb locus 62200 to 62350 (gene bank sequence HUM HBB__PREMRNA) with intron mutant IVS-1-6and the primers according to the invention.

FIG. 3 shows the calculated melting behavior of this nucleic acid obtained using the calculation scheme developed by Gerhard Steger et al. (Steger, G., Po, T., Kaper, J., and Riesner, D. (1987), Nucleic Acids Res. 15, 5085–5103). The segment represented in FIG. 2 includes the intron 1-β+ mutation IVS-1-6. The numbering corresponds to gene bank sequence HUM HBB__PREMRNA. The optimum probe for denaturing gels is based on the amplifying segment 62233–62340. The primer 1a* is constructed with a so-called G/C tail. BamH1 and EcoR1 restriction sites were selected for integration into the vector pBR322. Calculations for the different DNA denaturation states of β-globin segments at different temperatures for 1M NaCl are shown graphically. The melting diagram represented in FIG. 3 is to be understood as follows: the abscissa indicates the position of the nucleic acids, while the ordinate represents the probability of strand opening in relation to the specific nucleotide position. The third axis of the three-dimensional diagram corresponds to a temperature axis; here, it should be noted that the melting temperatures are depending on ionic strength of the medium as well. The probability of the opened-state of a base pair is calculated in steps of 0.5° C. The three-dimensional drawing illustrates the sequential denaturing behavior of various cooperatively denaturing regions. As is represented in FIG. 4, an internal loop having the size of one base pair at position 62302 decreases the melting temperature of the region with lowest stability.

FIG. 5 relates to the calculation of the temperature-dependent melting curve in integrated form (5a) and in differential form (5b), the symbol (*) denoting the curve of the wild type homoduplex, and (+) denoting the curve of the heteroduplex (Mv) as an A/C mispairing.

Figure 5A:
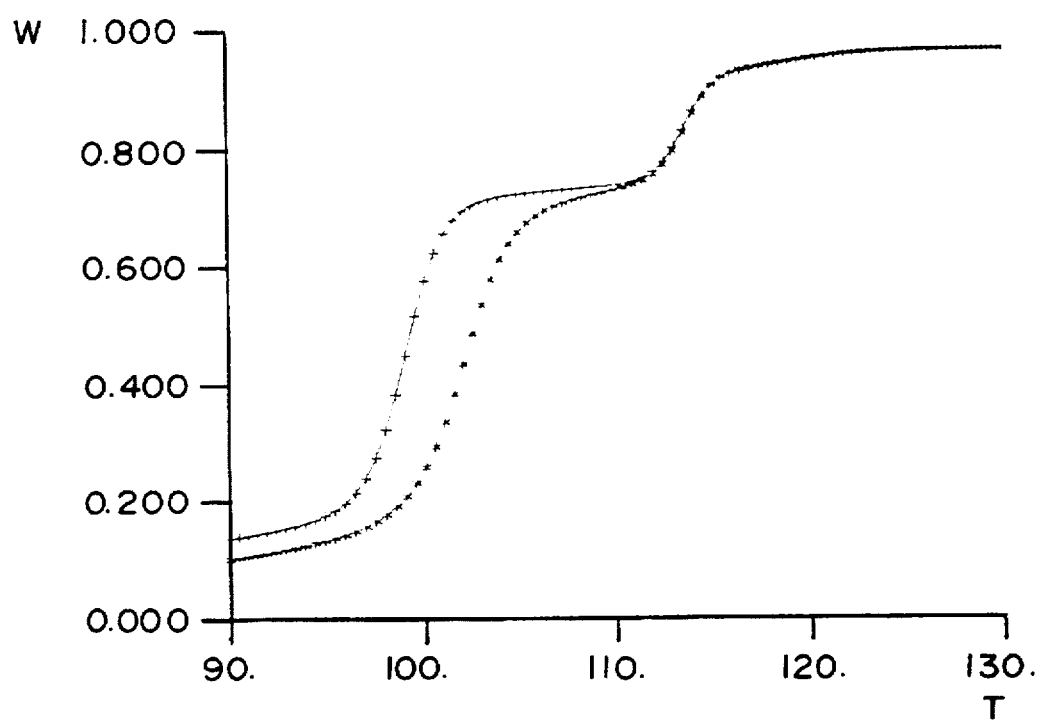
Figure 5B:
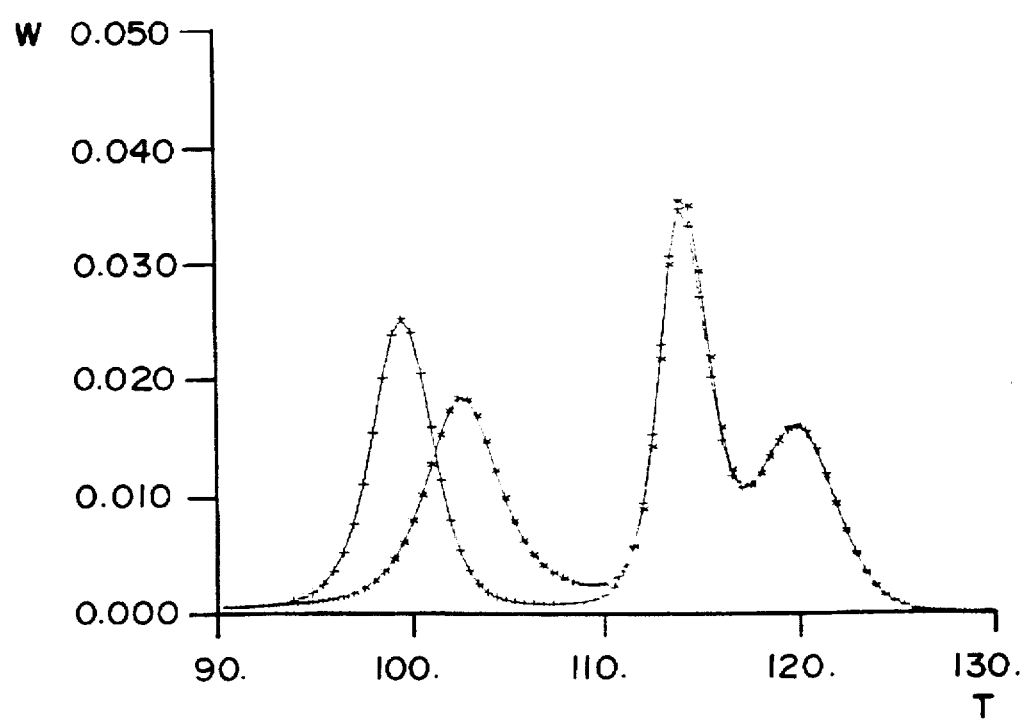

FIG. 5a shows the theoretically derived optical melting curve of the nucleic acid double strand of both the homoduplex and the heteroduplex (A/C). FIG. 5b shows the first derivation of the melting curve calculated in FIG. 5a. It is noted that the heteroduplex (+++) in the area of the thermodynamically labile region is significantly more destabilized due to mutation than the homoduplex (***) due to exponated internal loops in so-called mismatches. In this case, the melting point depression of this thermodynamically unstable region is about 4° C. as compared to the homoduplex.

Figure 6:
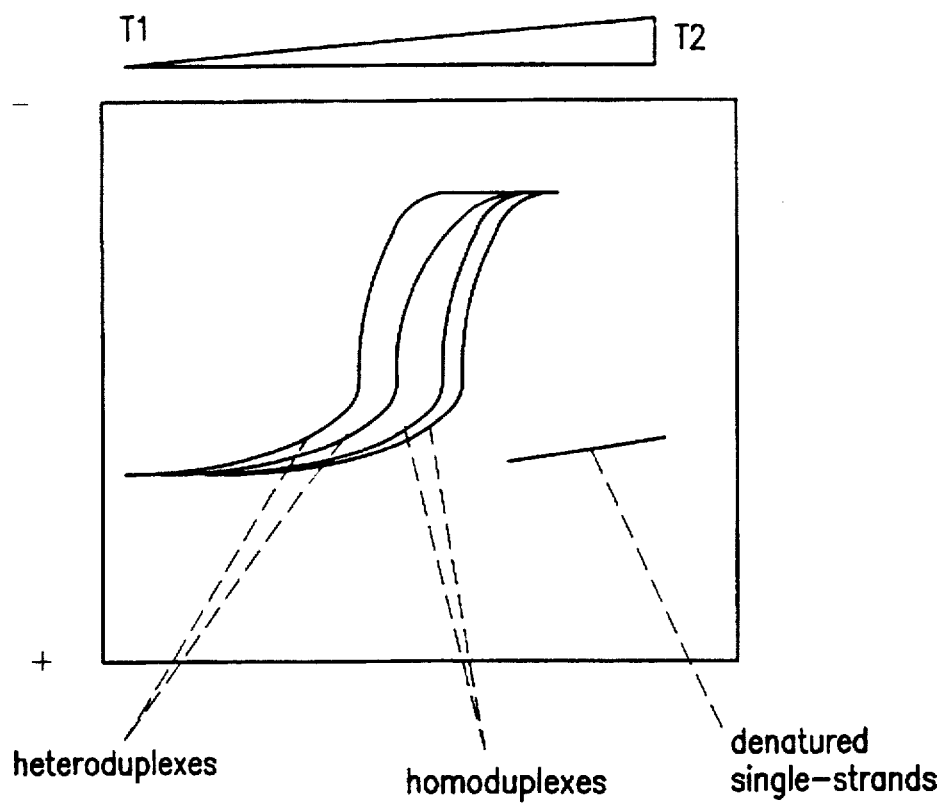

FIG. 6 shows the analysis of the amplified mutant segment with primer 1a*, primer 1b according to FIG. 2, and of the amplified wild type segment in vertical temperature gradient gel electrophoresis with a linear gradient of from 10° to 60° C. The fragments mixed equimolarly were applied subsequent to denaturation/renaturation. Heteroduplexes (Mv, Vm) and homoduplexes (Vv, Mm) were cleaved according to the schematic representation. A homozygous wild type DNA probe was PCR amplified using the primers 1a* as described above. The fragment was integrated between the BamH1/EcoR1 site of pBR322. A DNA sample of the homozygous mutant IVS-1-6 was amplified using BamH1 and EcoR1, cut, denatured, and hybridized using a cloned BamH1/EcoR1 fragment of the wild type gb sequence. The resulting homoduplexes (2 bands) and heteroduplexes (2 bands) are represented as four different bands. The Y-shaped conformations were stabilized by employing the G/C-rich oligonucleotide chain at the most stable end of the nucleic acid to be examined (cf., Myers, R. M. et al. (1985), Nucleic Acids Res. 13, 3131). When using parallel temperature gradient gel electrophoresis, the picture represented in FIG. 7 results with mutation IVS-1-6 in the sample material.

Figure 7:
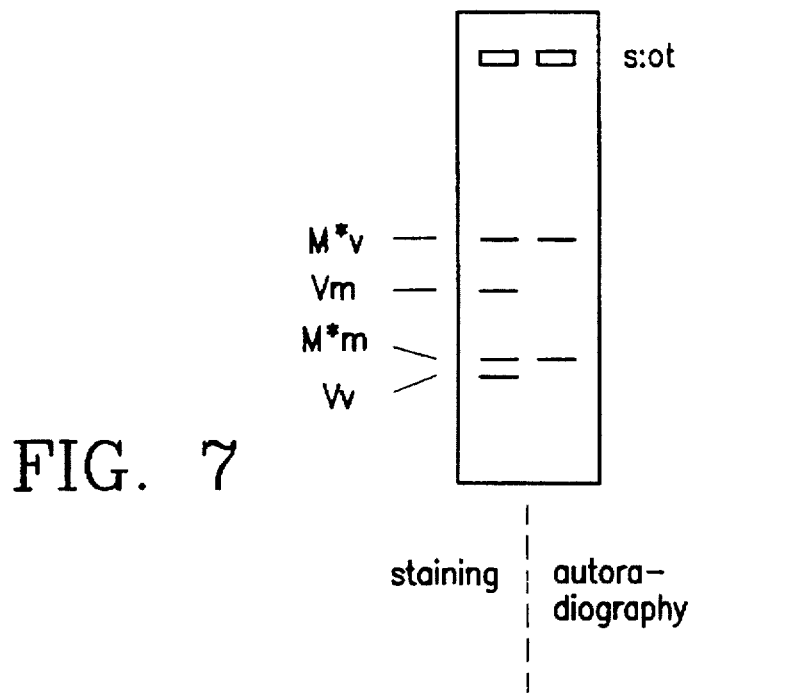

FIG. 7 shows the autoradiography of an analysis of different patient DNAs after amplification and test using the wild type standard (cf., FIG. 6, FIG. 2). The patient DNAs containing the IVS-1-6 mutation exhibit a second band. Since the test DNA contains only one marked strand, only two of these four bands contain the radioactive mark (cf., insertion in FIG. 7). The parallel temperature gradient runs between 25° and 65° C.

Figure 9:
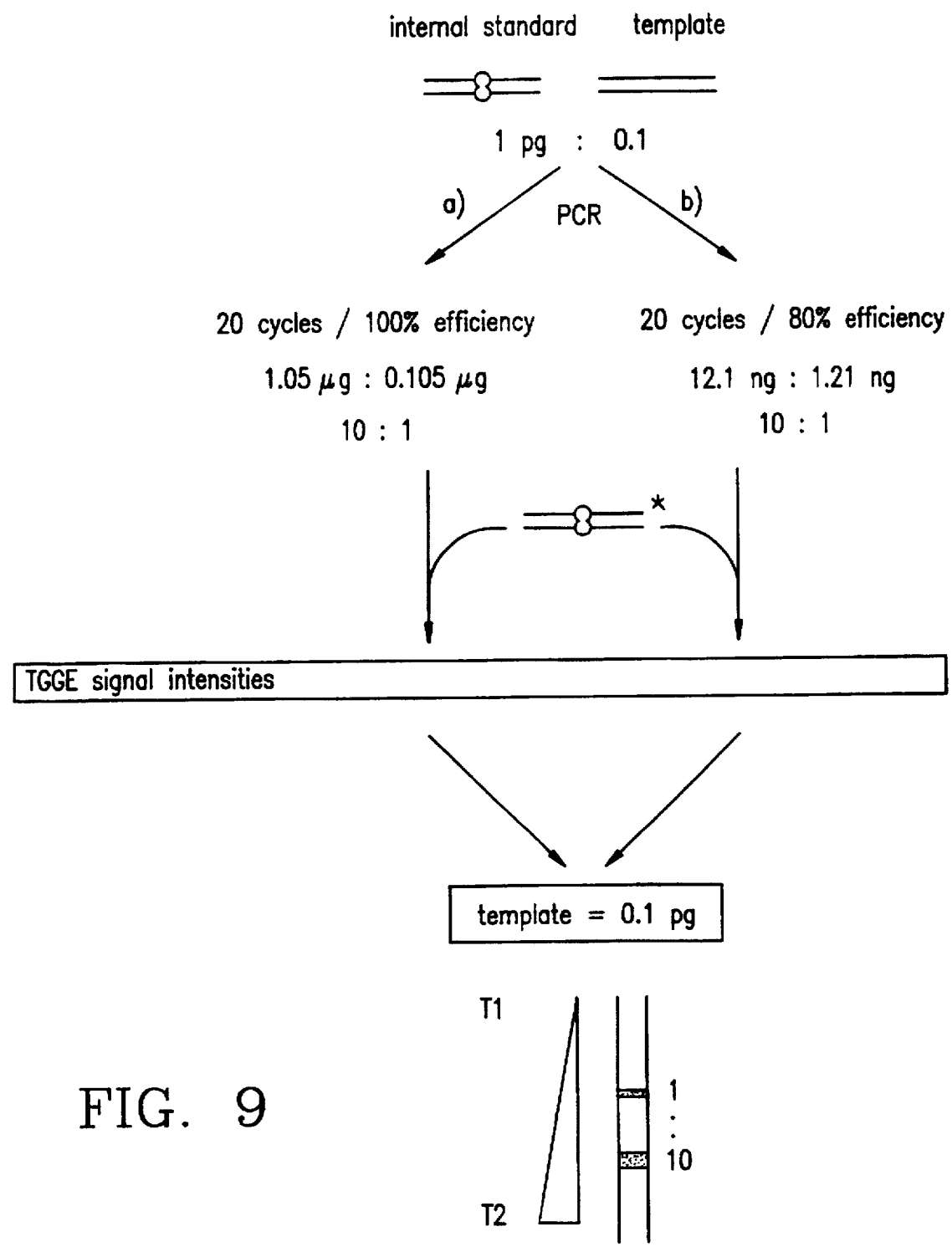

Additionally, the experiment shows that the mutant detection system is suited not only for qualitative but also for quantitative detection. The (radioactively) marked marker fragment (wild type) added in inferior molar amounts distributes proportionally on both the alleles after denaturation/renaturation. Mutation of one allele has no influence on the 1:1 distribution of the marker (FIG. 7). The marker itself contributes to the shift of the 1:1 distribution only below the experimental limit of error (±10%). Where the internal standard is not present in the mixture to be amplified, as is the case with the equally distributed alleles, it may be added externally. An internal standard of defined number of copies may serve to detect a template quantitatively if it differs from the standard in one mutation. Since exactly identical primers are employed, plateau effects, non-equal primer concentrations, or poor replication efficiency affect both components always in strictly symmetrical fashion. Where standard and target sequence to be measured do not differ more than by a factor of 100, preferably 10, the number of copies may be determined correctly via signal ratio (FIG. 9). In experimental terms, this approach represents a great simplification, since the polymerase chain reaction (PCR) may be continued to saturation without control.

FIG. 9 schematically represents the process described in FIG. 7. To the DNA to be amplified a standard of known concentrations (number of copies) is added, the standard differing in at least one mutation, e.g., a punctual mutation, from the nucleic acid to be analyzed. This mixture is subjected to an enzymatic amplification process until saturation occurs. Subsequently, an inferior amount of standard in marked form is added to the amplification mixture. Subsequent to at least one denaturation/re-naturation cycle, the mark, in number ratio of internal standard to target sequence to be quantified, is converted to the corresponding homoduplexes and heteroduplexes. Separation of homoduplexes and heteroduplexes is effected using temperature gradient gel electrophoresis. The ratio of signal intensity of the resulting bands, on multiplication with the number of standard copies, provides the amount of target sequence to be determined.

Use of a primer having affinity groups allows for particularly simple and effective sample preparation for the analysis of the nucleic acid to be examined. As the affinity groups, for instance, histidyl and biotinyl residues are possible. In the case of histidyl residues, two to eight histidyl residues are employed, with six being particularly preferred. Then, the chemically modified primer is fixed to a polymeric support via corresponding affinity groups. With histidyl-modified primer, a chelate complex of bivalent transition metal ions such as copper and nickel and nitrilotriacetic acid, bound to a polymeric support, is recommended. The free coordination sites of the transition metal ion are occupied by two histidyl residues. Since primer and histidyl residues are covalently bound to each other, the primer is bound to the polymeric matrix in this way. Complexes have been described for recombinant proteins (EP-A-0 282 042, EP-A-0 186 069) to NTA resins (EP-A-0 253 303). Where, for instance, biotinyl residues are covalently bound to the primer, a polymeric support having avidin molecules covalently bound is recommended.

As the polymeric supports, correspondingly modified membranes or correspondingly modified particles are possible. The polymeric support should have sufficient mechanical stability to stand pressure variations occurring during operation due to flow without damage. Now, when nucleic acids having mutations are amplified using the primer described, double-strands are formed which carry said affinity groups on one end (primer-mediated). Following sufficient amplification, the reaction mixture is reacted with the polymeric support and affinity moieties bound thereto such as nickel chelates or avidin molecules. In this fashion, sequences amplified by the primer are specifically bound at the surface of the solid support. This can be effected either in a batch process or in the form of a column filtration. By using this procedure, extraneous enzymes and reagents required for amplification are removed simply and mildly. Now, the amplified nucleic acid fragments bound to the matrix may be incubated in a simple manner using a marked, wild-type-derived nucleic acid probe. Using one or more denaturation/re-naturation cycles, heteroduplexes are formed which, subsequent to elution from the polymeric support such as by variation of buffer conditions or washing out using a competitor, may be subjected directly to analysis. The samples processed in this fashion may be subjected immediately to temperature gradient gel electrophoresis, for instance.

Figure 8:
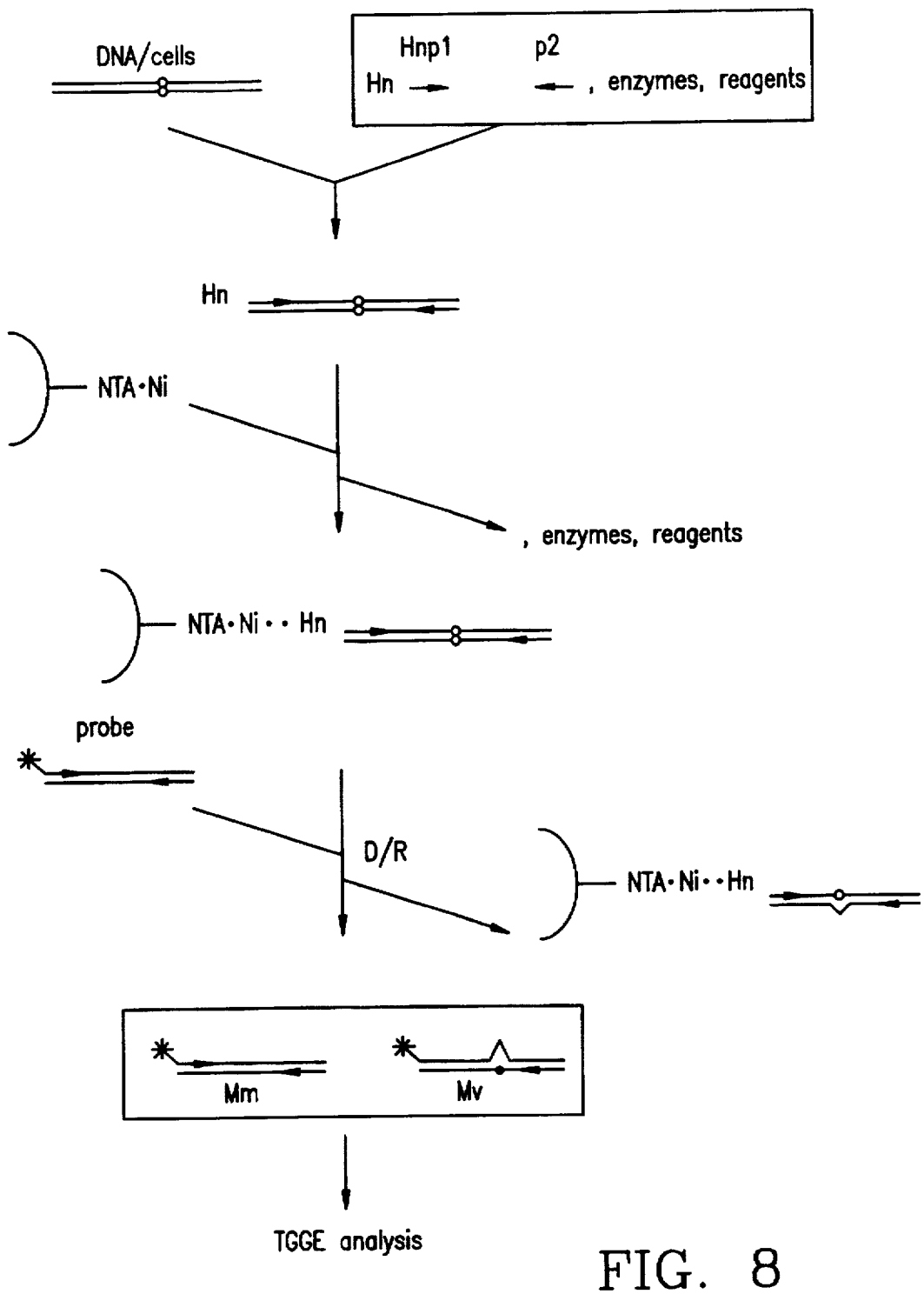

FIG. 8 represents a scheme according to the invention for temperature gradient gel electrophoresis-adjusted sample preparation. The primer Hnpl bears an oligohistidyl residue as a 5'-coupled side chain and thus, may be bound to solid phase supports bearing NTA ligands under neutral or alkaline conditions. In this step, contaminating enzymes and reagents are removed. After addition of reagent and optionally, internal marker substances, the denaturation/re-naturation cycle is passed. In this fashion, the framed structures Mm and Mv (marked homoduplex/marked heteroduplex) become available for temperature gradient gel electrophoresis analysis; that is, the second strand of the material to be analyzed is detected in the subsequent temperature gradient gel electrophoresis analysis.

The device according to the present invention particularly permits the process of the invention to be carried out. The device consists of at least two heating or cooling devices or one heating device and one cooling device to build up the temperature gradient. The heating or cooling devices are connected with heat reservoirs to ensure energy flow as required according to the process of the invention. The heat reservoirs and the heating or cooling devices are designed such that they completely surround a hollow body containing a separation medium. This hollow body contains in its lumen the separation matrix used for separation or the separation medium free of support. To build up the reproducible temperature gradient or, in an isothermal procedure, to ensure a reproducible uniform separation medium temperature level, the hollow body is surrounded by a thermostat jacket. The thermostat jacket may be connected, preferably in a thermally conducting fashion, with the heat reservoir or the heating or cooling devices.

In a preferred embodiment, the thermostat jacket may be formed by a metal plate provided with drillings into which the hollow bodies, preferably glass or plastic tubelets may be introduced. Preferably, two metal plates having parallel-running grooves are used, the recesses formed by the grooves after assembling the metal plates corresponding to the external shape of the hollow body used for separation, the metal plates being in direct heat contact.

FIG. 10 schematically shows the set-up of a preferred embodiment of the device according to the invention. FIG. 10a shows a cross-section along the line A—A of the hollow body having internally arranged a separation medium and being en-closed by a thermostat jacket.

FIG. 11 shows another preferred embodiment of the device according to the invention to build up a time temperature gradient.

Figure 12:
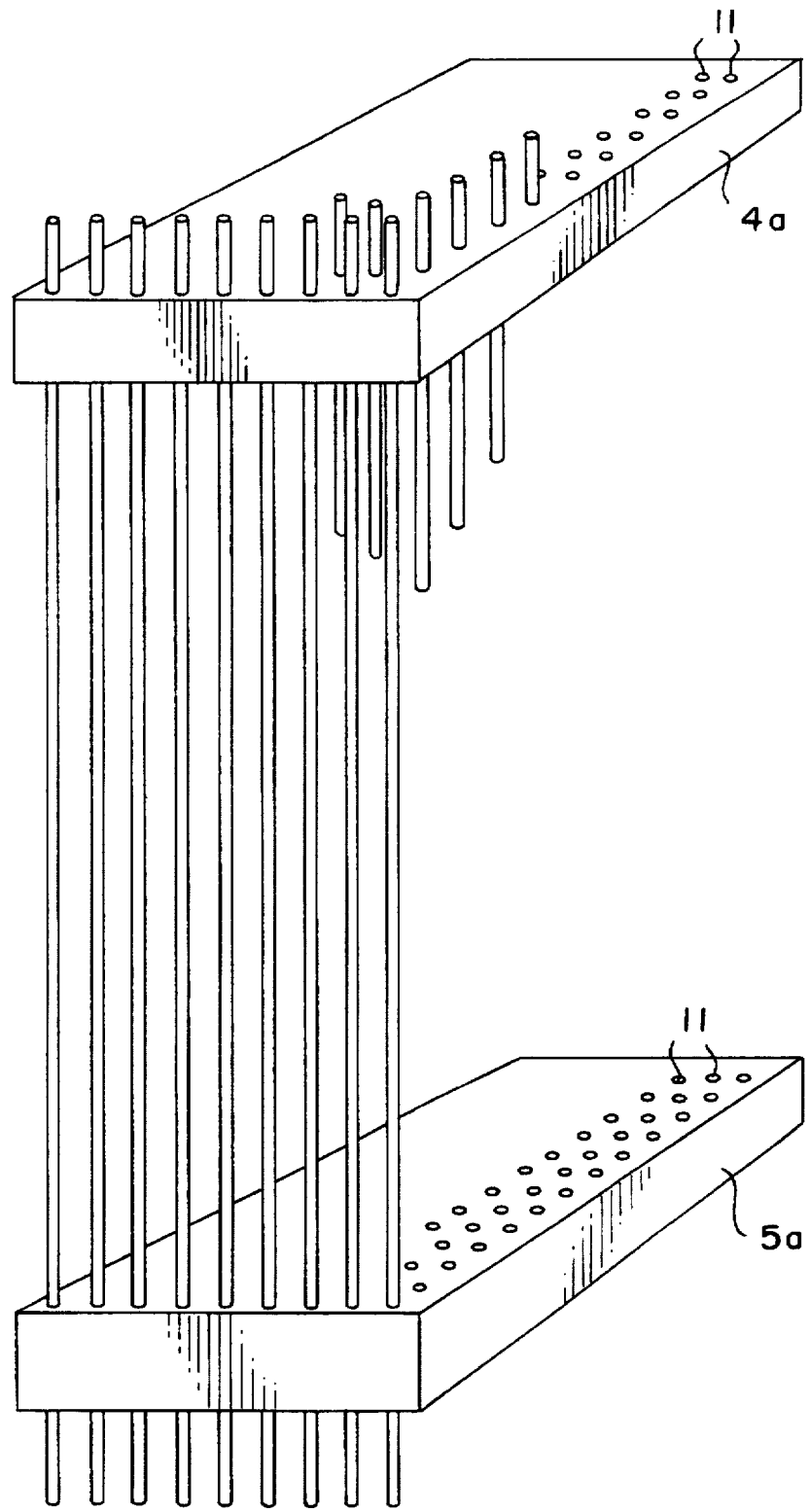

FIG. 12 schematically shows an embodiment of the device according to the invention capable of accommodating a multiplicity of hollow bodies used for separation.

FIG. 13 schematically illustrates the process course according to the invention using the device of FIG. 11.

Figure 14:
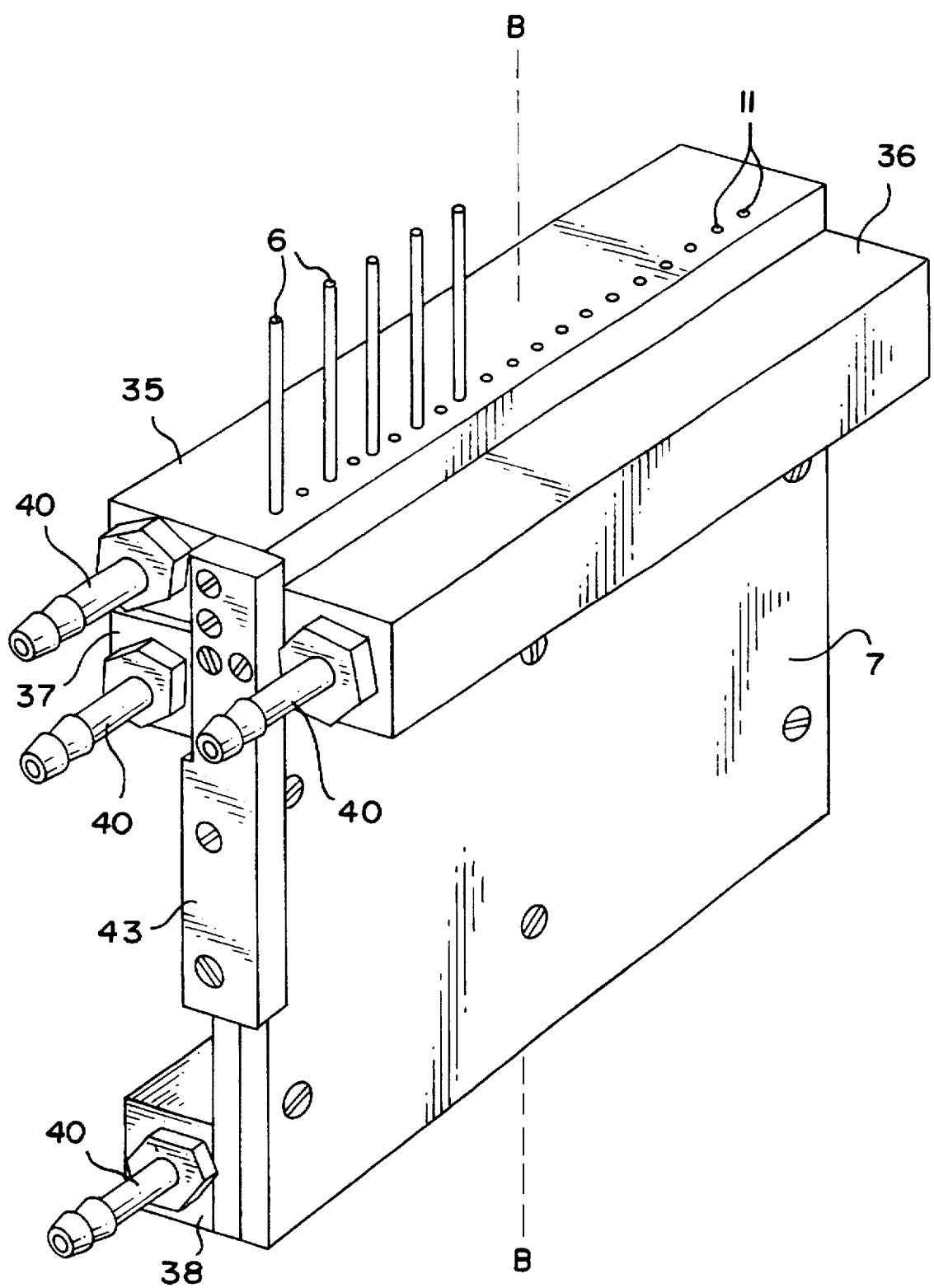
Figure 14A:
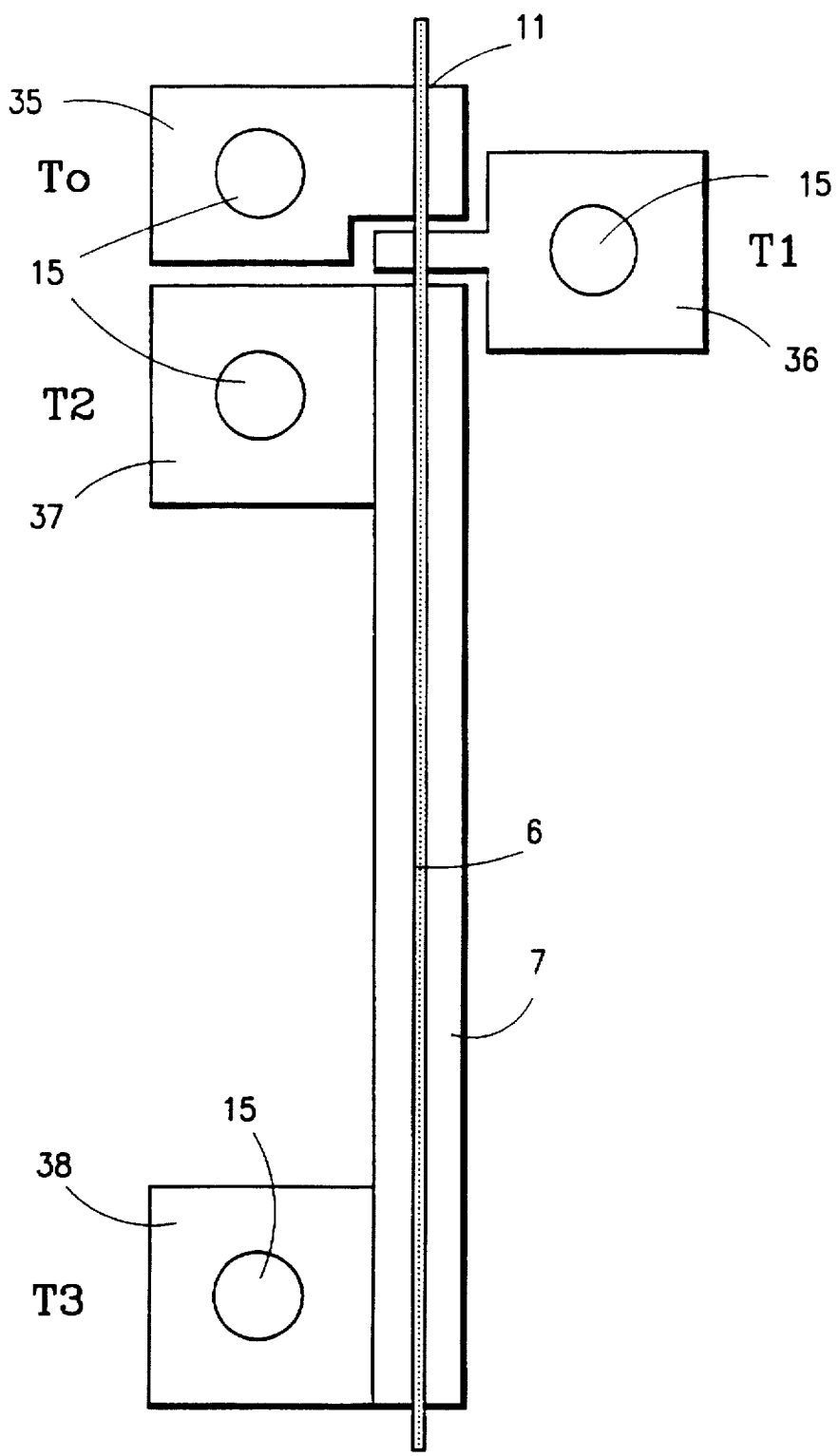

FIGS. 14 and 14a show a preferred embodiment of the device of the invention according to FIG. 12. Here, the thermostat jacket is formed by a metal plate consisting of two parts. The tube-shaped hollow body containing the separation medium is held in grooves running parallel in both plates.

Figure 15A:
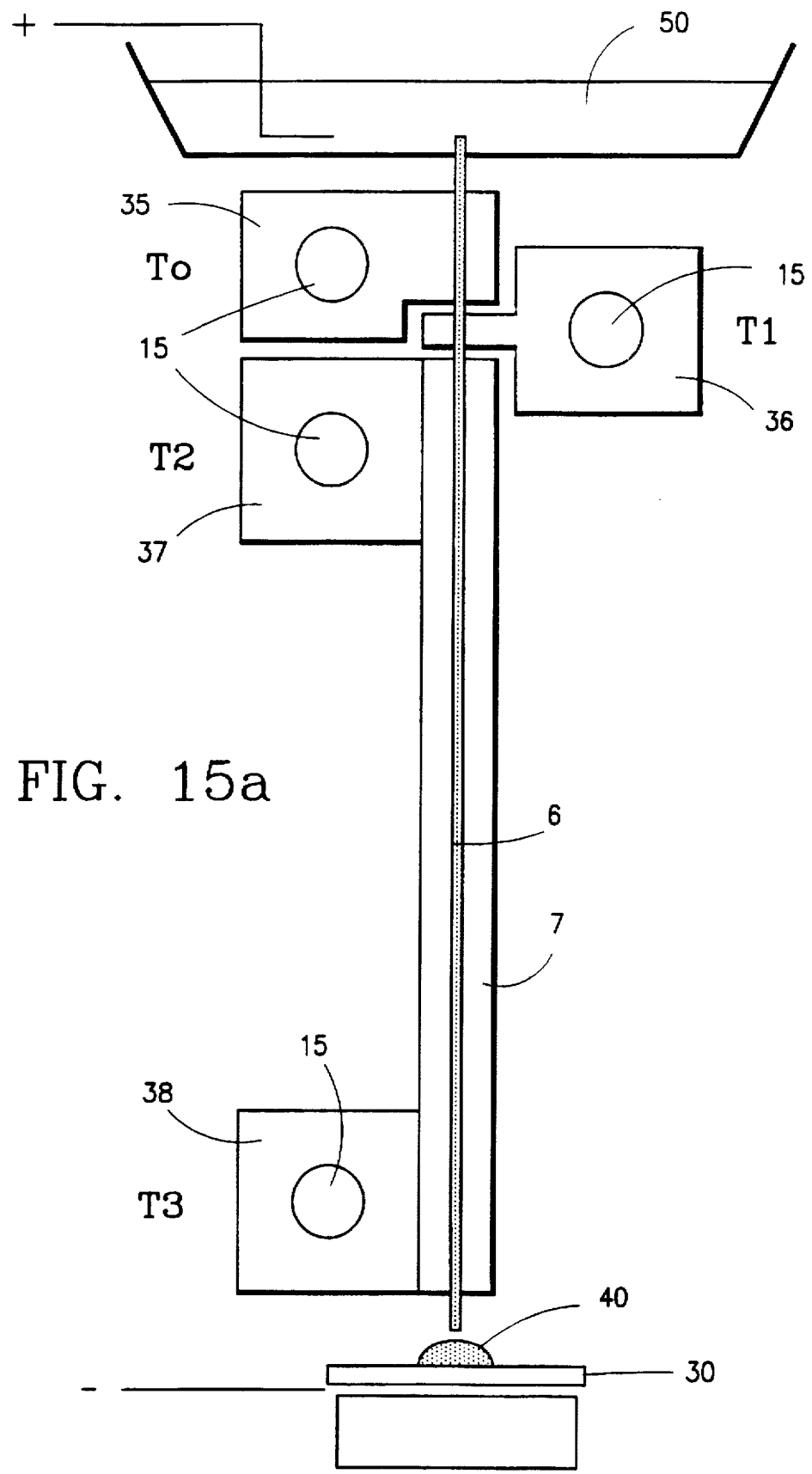
Figure 15B:
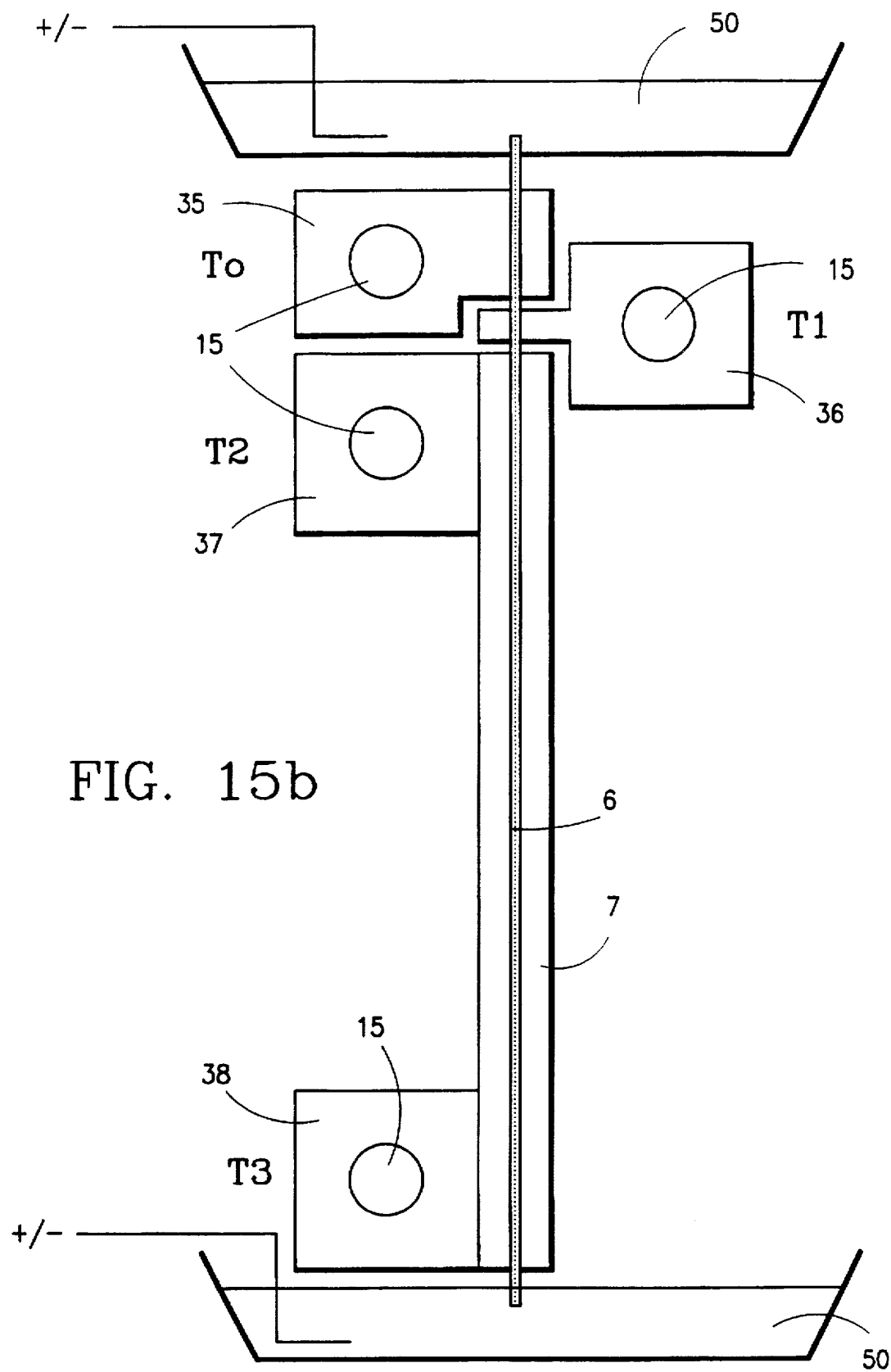

FIGS. 14a, 15a and b show a side cross-section of the device according to FIG. 14 along the line B—B. FIG. 15a schematically demonstrating sample intake as a momentary picture. FIG. 15b shows the device in a state ready for operation where the hollow body used for separation immerses both with top and bottom into a buffer reservoir 50.

The preferred embodiment represented in FIG. 10 consists of two heating and cooling devices 1, 2 of corresponding temperatures $T_2$ and $T_1$. These heating and cooling devices are connected with heat reservoirs 4, 5 in a conducting manner. Preferably, the heating and cooling devices as well as the heat reservoir are provided with centric drillings. Across these drillings, a hollow body 6 is arranged, preferably penetrating both sides. The hollow body 6 is enclosed by a thermostat jacket 7 from all sides. Preferably, the hollow body 6 is centered in the thermostat jacket 7. The hollow body 6 contains in its lumen the medium used for separation. Preferably, the thermostat jacket 7 consists of thermally conductive material, a material being particularly preferred which also the heat reservoirs are made of. The temperature levels 1, 2 are maintained by heating and cooling, respectively, preferably using Peltier elements, thermostattable fluid baths or electrical heatings 9. At the end of the separation path, a detection unit 10 is provided. FIG. 10a shows the situation in cross-section along the line A—A. Preferably, the interspace between the outer wall of hollow body 6 and the inner wall of thermostat jacket 7 is filled with a viscous liquid 8. The separation medium completely fills the cross-section of hollow body 6. Preferably, the hollow body 6 is of cylindrical shape, particularly preferred is a capillary. The temperature present at any position of the separation path may be calculated according to the formula $$T=T_2-(T_2-T_1)\cdot d_2/(d_1+d_2);$$

herein, $d_1$ represents the distance of the position from temperature $T_1$, and $d_2$ represents the distance of the position from temperature $T_2$ which temperatures are present at each temperature level 2, 1.

FIG. 11 shows a preferred embodiment for conducting the process of the invention as an electrophoresis superimposed by a time temperature gradient. It consists of three temperature levels 1, 2, 3 which again are preferably connected with heat reservoirs. The components, namely hollow body 6, heat exchange jacket 7, detection unit 10, heating and cooling device 9 are similar in design to the device of FIG. 10, with the only exception that thermostat jacket 7 is connected to the heat reservoir of the heating and cooling device at temperature level 2 in thermally non-conducting fashion.

Figure 13A:
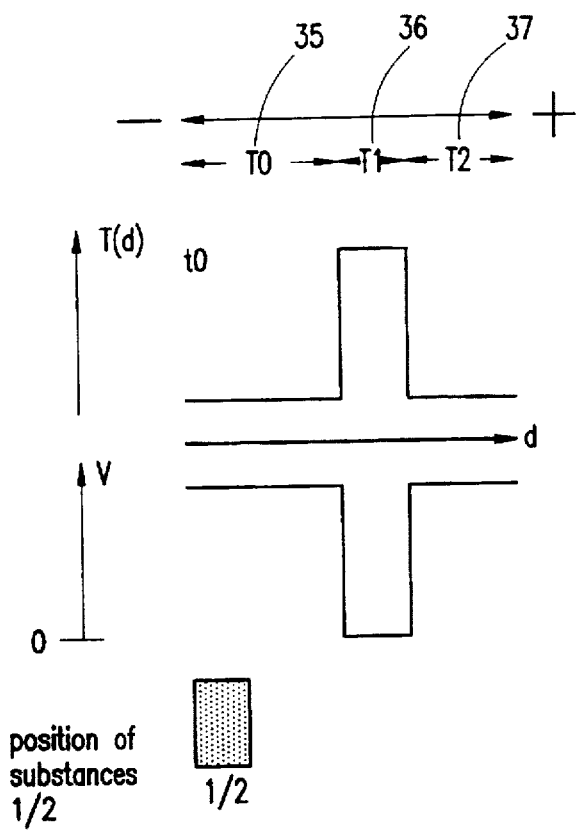
Figure 13B:
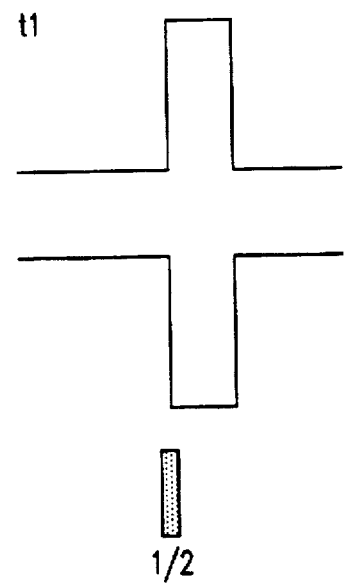
Figure 13C:
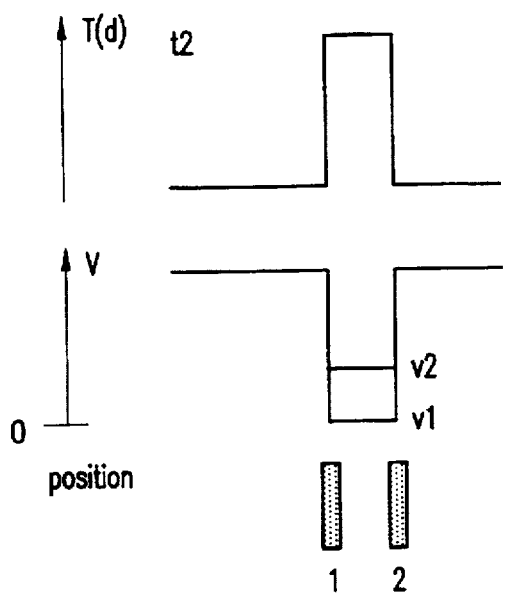
Figure 13D:
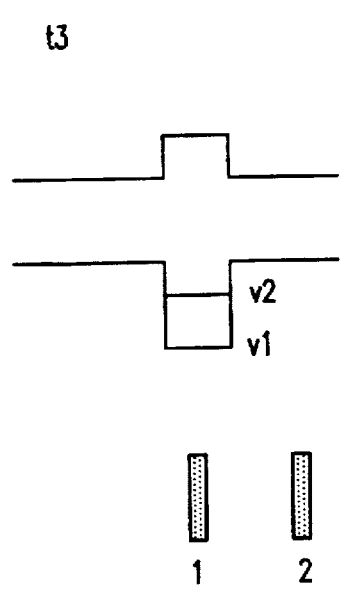

FIGS. 13a to 13d show the course of the process as is conducted, for instance, using a device according to FIG. 11. The gradient of the electric field used for separation is plotted in abscissa direction and at the same time symbolizes any position of the separation path to be passed. Once, on the ordinate in positive direction, the temperature levels depending on position are marked (FIG. 13a). The migration velocity of the sample components to be separated is represented by the step function beneath the temperature curve. For example, the migration velocity (V) at $T_1$ ($t_0$) is approximately equal to zero. The sample is applied at temperature level $T_0$ which in this case, for simplicity, shall be equal to temperature level $T_2$ at the end of the electrophoresis separation path. Once applied, the substances 1 and 2 occupy the volume given by the spots in the designated position. The sample migrates along the field gradient in the separation medium until it reaches temperature level $T_1$. If, for instance, the sample consists of nucleic acids, they are subject to denaturation here by widening of the double-strand to so-called loops. As a consequence, the migration velocity is reduced. The sample is concentrated at the boundary between $T_0$ and $T_1$. This situation is represented in FIG. 13b in the form of lower volume (time $t_1$). Now, the temperature of temperature level $T_1$ is decreased as a function of time. The thermodynamically more stable fraction, denoted as fraction No. 2 in FIG. 13c, then closes the double-helix and gains higher mobility. As a consequence, this fraction begins to migrate in the separation medium. FIG. 13d shows the situation at a time $t_3$ where the temperature T has decreased so far that the thermodynamically more unstable sample, denoted as No. 1 here, likewise begins to migrate across the separation medium. During this time interval, component No. 2, however, has been passing a considerable part of the separation path or, with corresponding dimensioning, has already left the same, at which point it may be detected.

This embodiment preferably uses a very short capillary including separation medium and may be thermostatted at three regions ($T_0$, $T_1$, $T_2$) thermally separated from each other. The partial denaturation occurring at the temperature boundary between $T_0$ and $T_1$ of, for instance, nucleic acids to form internal loops may be supported by appropriate reagents.

At the boundaries of the individual temperature levels, however, the temperature boundaries become diffuse, so that the representation of FIG. 12 is to be understood merely as an idealized rectangular shape of temperature and migration velocity. To ensure a temperature level boundary as sharp as possible in spite of this, the temperature levels $T_2/T_1/T_0$ preferably are connected such that heat is not conducted.

This procedure of the invention may also be realized by using flat separation media which are thermostatted as is described for simple spatial temperature gradients in the German patent application P 36 22 591.

FIG. 12 shows a preferred device characterized in that heating and cooling devices 1, 2 having corresponding heat reservoirs 4, 5 are capable of accommodating a multiplicity of hollow bodies 6 in that the devices 1, 2 and 4, 5 are designed in the form of blocks—4a, 5a —and have a multiplicity of drillings 11 across which the hollow bodies 6 are arranged projectingly, preferably projecting from an end side. This device is advantageous in that using one device, a large number of analyses may be carried out with the object of detecting known or unknown mutations. The device ensures that several samples may be analyzed simultaneously using thermostatting by various thermostat elements but with each one common heating or cooling system. A preferred embodiment is adapted to the format microtiter (96 well) in the sense of multichannel systems, preferably 8 or 12, or a 96 channel system. As read-out systems, preferably, fluorescence-marked nucleic acid probes are utilized which may be recorded optically at the front and/or the end of the thermostat device as a function of separation time and in stationary fashion using commercially available detection systems. Thus, by using appropriate reagent kits, mutations in genetic material may be evaluated automatically.

Thermal equilibration of each heating or cooling device may be effected homogeneously electrically via heating wires, preferably, however, via Peltier elements. Likewise, liquid heating devices in the form of thermostattable liquid baths are possible. However, care is to be taken here that the heating or cooling devices connected to the thermostattable jackets of the capillary have, at each transition site, nearly identical temperatures with respect to all jackets. This may be realized by symmetrically constructed Peltier heating/cooling or, in the case of liquid thermostatting, by counter-current channels, with the sum of temperatures of opposite flows remaining nearly identical at each capillary position.

The temperature gradient gel electrophoresis designed according to the invention is particularly suited for modes of action where the temperature gradient is not dimensioned spatially but is built up time-variably or in the form of a time gradient. This means that a heating or cooling reservoir is controlled by a time-defined temperature program whereby, in the end, mobilities of the molecules to be separated may be controlled as an action of time. Thus, for example, an open circular nucleic acid or a partially denatured double-strand nucleic acid as well may be virtually "locked" in the gel at high temperatures and mobilized in the separation medium only after a certain period of time elapsed by reducing the temperature subsequent to reversible structure regeneration. This holds for the separation in capillaries and on flat supports. The advantage of this technique is that here. extremely short separation paths may be realized.

The schematic FIGS. 15a and b show a preferred device for performing the process of the invention wherein, according to FIG. 14. 12 samples may be analyzed simultaneously. Notably, a total of 4 temperature levels $T_0$ to $T_3$ may be controlled variably. Using this preferred device. spatial, timewise as well as combinations of spatial and timewise gradients may be built up. This device of the invention is particularly suited to optimize parameters in the laboratory for the separation of samples to be analyzed.

FIG. 14 shows a preferred embodiment of the device according to the invention. There is present a total of 4 controllable heating and cooling devices (35 to 38), respectively. The temperature levels $T_0$ to $T_3$ may be controlled independently. Temperature is adjusted by introducing. via inlets 40, appropriately thermostatted liquids into the temperature reservoirs designed as metal blocks here. Opposite to the feed inlets 40, the liquids used for thermostatting are led away via corresponding outlets (not shown in the drawing). The metal block forming temperature level 35 is provided with drillings where the hollow bodies 6 used for separation may be pushed through. The metal plate 7 forming the thermostat jacket is constructed of two parts preferably being screwed together. This plate is provided, at opposite positions each, with cut grooves adjusted to the diameter of hollow body 6. The metal blocks 35 to 38 providing the corresponding temperature levels are connected to the thermostat 7 by screws via connection 43.

FIG. 14a shows a cross-section along the line B—B of the device drawn in FIG. 14. The hollow body 6 serving for separation completely penetrates the hollow bodies 7 forming the thermostat jacket. Preferably, a viscous liquid is present in the interspace formed between hollow body 6 and thermostat jacket 7. The metal blocks 37 and 38 are connected in thermally conductive fashion with the thermostat jacket 7 via direct contact of the planar side planes. Preferably, the blocks 37, 38, and the thermostat jacket are made of the same material. In a special embodiment these elements of the device according to the invention are made of a single piece. The metal blocks building up temperature levels $T_0$, $T_1$ are, together with the thermostat jacket comprising hollow body 6, made of a single piece, for instance. The metal blocks 35, 36 building up temperature levels $T_0$, $T_1$ are bored. The drillings in the various metal blocks and in the thermostat are made coincide, so that hollow body 6 used for separation may be pushed through the device built up by the individual elements 35, 36, 37, and 38. The metal blocks 35 to 38 are provided with drillings 15 (cross-section) through which the liquid used to build up each temperature level is flowing.

It will now be described how to separate the mixture of marked hybrids representing a homoduplex and a heteroduplex (one base mismatch) described in the figure description of FIG. 2 and 3. The two cloned inserts (wild type and IVS-1-6) described in the figure description of FIG. 2 and 3 were mixed in the form of their EcoR1/BamH1 digested plasmids (45 ng each). These were admixed with radioactively marked insert in limited amount (9 ng based on plasmid), the radioactivity marker being incorporated by 32P-dATP, dCTP, dGTP, dTTP incorporation using polymerase-1 Klenow fragment. The specific activity was about $10^6$ cpm/pmole restriction site. The mixture was denatured in 55 µl buffer 10 mM Tris, 1 mM EDTA, pH 7.5 at 98° C. for 2 minutes and, after adjusting to 250 mM NaCl, was renatured at 50° C. for one hour. DNA was precipitated using 2.5 vols. ethanol at −20° C. for 30 minutes, washed with 80% ethanol and dried. The sample was taken up in 0.01·TBE bromophenol blue. 13,000 cpm in 3 µl were charged as drop 40 onto a planar platinum electrode (FIG. 15a 30). Sample application was effected electrophoretically after immersion of the cathode side capillary by applying a voltage of 100 V against the grounded platinum cathode 30 (FIG. 15a) for two minutes each. As the TBE buffer (89 mM Tris, 89 mM boric acid, 2.5 mM EDTA, pH 8.3) has high buffer capacity in the direction of high pH values, the alkalinity of the sample, in spite of low buffer concentration (0.01·TBE), will not increase by more than one pH unit (pH 8.3 to 9.3). In this fashion, about 50% of the marked nucleic acid is taken up by the gel.

As the capillaries, filled glass capillaries with 5% polyacrylic amide gel and an internal diameter of 0.45 mm were used. Buffer conditions were selected to be 0.1·TBE, 4M urea. FIG. 15b schematically shows the device of the invention in electrophoresis operation. Once sample application has been effected, both ends of capillary 6 are contacted with each 100 ml buffer reservoir 50.

a) The sample was separated in a spatial gradient ($T_3=30°$ C., $T_2=70°$ C.).

The table shows the difference of migration paths in cm of the homoduplex compared to each migration path of the heteroduplex. In the expected temperature interval of 40° C. to 50 C., the experimentally desired separation of signals results.

| Electrophoresis time (min) | Difference of capillary gel position (mm) of wild type fragment and IVS-1-6 fragment |
|---|---|
| 30 | 0 |
| 42 | 0 |
| 54 | 0 |
| 66 | 0 |
| 78 | 2 |
| 90 | 4 |
| 102 | 6 |
| 114 | 6 |
| 126 | 7 |
| 138 | 7 |
| 150 | 9 |
| 162 | 11 |

The data is based on single measurement in separated capillaries.

b) Analogous to the mode of action of FIGS. 13a to d, the sample was applied on the side $T_0$ ($T=T_2 37=T_3=30°$ C.), and the separation was conducted over the 4 mm separation path of temperature $T_1$. Only the samples having passed $T_1$ within the temperature interval (40<$T_1$ <50) will be separated.

According to the invention, the temperature level of $T_1$ was decreased in linear fashion during electrophoresis. The samples reaching $T_1$ just below that temperature where dissociation to single-strands occurs (50° C.) are separated in section $T_1$ 36 (4 mm separation path) into bands in a relative distance of up to 1 cm.

Combination of spatial and timewise gradients of temperature which cannot be achieved by using a static chemical gradient system, is of great practical importance for some applications. Two applications shall be exemplified. They will be explained schematically in FIG. 16.

a) Fragments having highly different native migration velocity due to, for example, strongly differing fragment size, can be analyzed together only with difficulty. In some cases the rapidly migrating small fragment 60 (fragments and their corresponding gel positions are represented as small bars) is already subject to strand separation while the large fragment 70 has not yet reached the temperature of beginning denaturation. According to the invention, the high temperature $T_2$ is adjusted such that separation of the most stable double-helix section or the G:C clamp does not yet occur. During electrophoresis the temperature $T_1$, however, is adjusted from low temperature to steadily increasing temperature, at maximum until $T_1=T_2$ is reached. In this way, each molecule passes the temperature gradient, regardless of its migration velocity or size.

b) Renaturation experiments as schematically described in FIGS. 16b and 16c provide sharp band signals only in cases where not merely a spatial temperature gradient alone is passed. Indeed, in this case an undesired effect of band broadening occurs in foldback which is all the more disturbing, the steeper the course of the denaturation curve. In this case, the front of the band will be strongly accelerated with respect to the end, since lower temperatures are present behind. As a result, the band is blurred. On the contrary, this effect is very desirable where, vice versa, the band front in migration direction migrates relatively at higher temperatures. According to the invention, this may be achieved also with renaturation experiments by combining space and time gradients. Instead of renaturation in a linear T gradient as conducted, e.g., using a device according to FIG. 1, the sample may be subjected to electrophoresis and analyzed in a relatively increasing gradient between $T_1$ and $T_2$ (FIG. 10) within the time interval $t_0$ to $t_3$ (FIGS. 16b and c), both temperatures, however, being jointly decreased (FIG. 16b), or only $T_1$ is decreased (FIG. 16c) to an extent that the sample having shorter running time experiences lower temperature, the band front, however, always has higher temperature than its rear side. In this way, bands grow sharper according to the invention.

The process according to the invention and the device of the invention may be used for analytical detection and quantitative detection as well as for preparation of components from material mixtures. Analysis and preparation may be performed simultaneously with many samples; detection and evaluation may be effected automatically. In particular, process and device are suited for preparation and analysis of viroids, viral nucleic acids, satellite RNA, for analysis of mutations in nucleic acids, for analysis of mutations in proteins, and for analysis of protein nucleic acid complexes.

Temperature gradient gel electrophoresis proves particularly advantageous for the preparation of variants, since direct sequencing of variants is possible without prior cloning. This is permitted by elution of exceedingly small amounts of a specific variant subjected to enzymatic amplification and subsequent sequencing. Such modes of operation will gain importance in future, since working with vectors otherwise used for amplification, and working with recombinant organisms is hampered by safety injunctions.

We claim:

1. A process for the quantitative and qualitative detection of mutants or specific gene sequences comprising the steps of:
   a) adding, to a mixture of different nucleotide sequences, in which one of the different nucleotide sequences has a known concentration, a marker-carrying nucleic acid sequence, the sequence of which is identical to one of the nucleotide sequences, in an amount less than said known concentration, wherein the marker can emit a detectable signal;
   b) subjecting the mixture to at least one denaturation/renaturation cycle to obtain hybrids of the different nucleotide sequences with the marker-carrying nucleic acid sequence;
   c) analyzing the mixture to detect a mutant or a specific gene sequence by separating nucleic acids in the mixture, using (i) time-controlled temperature gradient gel electrophoresis, wherein the temperature gradient is built up by varying the temperature with time, or (ii) a combination of the time-controlled temperature gradient gel electrophoresis and spatial-controlled temperature gradient gel electrophoresis and examining the separated nucleic acids for the marker signal and measuring relative intensities of detected signals.

2. The process according to claim 1, wherein the marker-carrying nucleic acid sequence hybridizes to the nucleotide sequence having a known concentration.

3. The process according to claim 1, wherein the mixture of different nucleotide sequences has been obtained by enzymatic amplification.

4. The process according to claim 1 using the combination of time-controlled and spatial-controlled temperature gradient gel electrophoresis, wherein the temperature gradient is oriented perpendicularly to the direction of the electrical field.

5. The process according to claim 1 using the combination of time-controlled and spatial-controlled temperature gradient gel electrophoresis, wherein the temperature gradient is oriented parallel to the direction of the electrical field.

6. The process according to claim 1, wherein one of the different nucleotide sequences is a mutation-carrying nucleotide sequence, which forms a heteroduplex with the marker-carrying nucleic acid sequence such that the mutation is located in a thermodynamically unstable region of the heteroduplex.

7. The process according to claim 5, wherein the time-controlled temperature gradient sets off, at the cathode side of the electrical field, from a temperature level higher than the melting point of the thermodynamically unstable region of the heteroduplex and is time-controlled in the direction of decreasing temperature toward the anode side of the electrical field.

8. The process according to claim 1, wherein the spatial-controlled temperature gradient is oriented perpendicularly to the direction of the electrical field.

9. The process according to claim 1, wherein the spatial-controlled temperature gradient is oriented parallel to the direction of the electrical field.

10. A process according to claim 1, wherein the anode side temperature level of the spatial-controlled temperature gradient is higher than the temperature level at the cathode side.

11. A process according to claim 1, wherein the cathode side temperature level of the spatial-controlled temperature gradient is higher than the temperature level at the anode side.

12. A process according to claim 1, wherein the sequence having a known concentration is the nutation-bearing sequence.

* * * * *